United States Patent
Cai et al.

(10) Patent No.: US 12,403,473 B2
(45) Date of Patent: Sep. 2, 2025

(54) PARTICLE SORTER, PARTICLE SORTING METHOD, AND MICRO FLOW PATH CARTRIDGE

(71) Applicant: SYSMEX CORPORATION, Kobe (JP)

(72) Inventors: Kunpeng Cai, Kobe (JP); Shruti Mankar, Kobe (JP); Anastasia Maslova, Kobe (JP); Taiga Ajiri, Kobe (JP); Yumiko Sakai, Kobe (JP); Shunsuke Watanabe, Kobe (JP); Tasuku Yotoriyama, Kobe (JP); Ayato Tagawa, Kobe (JP); Takehiro Hasegawa, Kobe (JP); Yoshiaki Miyamoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1050 days.

(21) Appl. No.: 17/349,656

(22) Filed: Jun. 16, 2021

(65) Prior Publication Data
US 2021/0394184 A1    Dec. 23, 2021

(30) Foreign Application Priority Data
Jun. 19, 2020   (JP) ................. 2020-105774

(51) Int. Cl.
    *B01L 3/00*    (2006.01)
    *C12Q 1/02*    (2006.01)
    *G01N 35/10*   (2006.01)

(52) U.S. Cl.
    CPC ... *B01L 3/502761* (2013.01); *B01L 3/502738* (2013.01); *B01L 3/567* (2013.01);
    (Continued)

(58) Field of Classification Search
    CPC ................. B01L 2200/0652; B01L 2400/0655
    See application file for complete search history.

(56) References Cited

U.S. PATENT DOCUMENTS

| | | | |
|---|---|---|---|
| 4,756,427 A | | 7/1988 | Gohde et al. |
| 5,427,946 A | * | 6/1995 | Kricka ................. B01J 19/0046 435/259 |

(Continued)

FOREIGN PATENT DOCUMENTS

| | | |
|---|---|---|
| EP | 1065378 A2 | 1/2001 |
| EP | 2191895 A1 | 6/2010 |

(Continued)

OTHER PUBLICATIONS

Mechano Transformer Corporation, "What is MechaTrans®?" Web page <https://www.mechano-transformer.com/en/ technology/01_about.html>, retrieved from Internet on Jun. 10, 2021.

(Continued)

*Primary Examiner* — Natalia Levkovich
(74) *Attorney, Agent, or Firm* — Crowell & Moring LLP

(57) ABSTRACT

To shorten the time required to sort target particles with sufficient purity, a particle sorter is provided. A particle sorter 200 including a micro flow path cartridge 10 having a first flow path 10 with a detection area 11 and a sorting area 12, a second flow path 20 for returning the target particle-containing sample 81 upstream from the detection region 11 of the first flow path 10, an installation unit 110 of the micro flow path cartridge 100, a liquid feeding unit 120, a detection unit 130 that outputs a signal corresponding to the target particles 91 passing through the detection region 11, a sorting mechanism 140 configured to perform a sorting operation of the target particle-containing sample 81 in a sorting region 12 based on the signal from the detection unit 130, and a control unit 150 for controlling the liquid feeding unit 120 so as to return the sorted target particle-containing (Continued)

sample 81 upstream of the detection region 11 of the first flow path 10 via the second flow path 20, and controlling the sorting mechanism 140 so as to perform a sorting operation on the returned target particle-containing sample 81.

14 Claims, 18 Drawing Sheets

(52) U.S. Cl.
CPC ............ *C12Q 1/02* (2013.01); *G01N 35/1009* (2013.01); *B01L 2200/0652* (2013.01); *B01L 2300/0816* (2013.01); *B01L 2300/123* (2013.01); *B01L 2400/0415* (2013.01); *B01L 2400/0655* (2013.01)

(56) References Cited

U.S. PATENT DOCUMENTS

| | | | |
|---|---|---|---|
| 5,587,128 A * | 12/1996 | Wilding | B01L 3/502715 |
| | | | 435/6.12 |
| 10,513,679 B2 | 12/2019 | Tabata et al. | |
| 2010/0137163 A1 | 6/2010 | Link et al. | |
| 2015/0064694 A1 | 3/2015 | Sadri et al. | |
| 2018/0133715 A1 | 5/2018 | Craig et al. | |
| 2018/0298324 A1 | 10/2018 | Takeda et al. | |

FOREIGN PATENT DOCUMENTS

| | | |
|---|---|---|
| JP | H7-242003 A | 9/1995 |
| JP | 2014-29327 A | 2/2014 |
| JP | 5845533 B2 | 1/2016 |
| JP | WO2016/182034 A1 | 3/2018 |
| JP | 2019-50778 A | 4/2019 |
| WO | 2018/067915 A1 | 4/2018 |
| WO | 2018/134311 A1 | 7/2018 |
| WO | 2018/148194 A1 | 8/2018 |
| WO | 2018/174748 A1 | 9/2018 |

OTHER PUBLICATIONS

Mechano Transformer Corporation, "Application of MechaTrans®" Web page <https://www.mechano-transformer.com/en/technology/03_applications.html>, retrieved from Internet on Jun. 10, 2021.

Mechano Transformer Corporation, "Piezo Actuator : MechaTrans®" Web page <https://www.mechano-transformer.com/en/products/mechatrans/index.html>, retrieved from Internet on Jun. 10, 2021.

S. Sakuma et al., "On-chip cell sorting by high-speed local-flow control using dual membrane pumps", Lab on a Chip, Aug. 21, 2017, pp. 2760-2767, vol. 17, No. 16, The Royal Society of Chemistry.

Technical Specification Sheet of The Cyto-Mine® Single Cell Analysis and Monoclonality Assurance System, 2 pages, Sphere Fluidics Limited, Cambridge, UK dated May 10, 2017.

L. Mazutis et al., "Single-cell analysis and sorting using droplet-based microfluidics", Nature Protocols, Apr. 2013, pp. 870-891, vol. 8, No. 5, Nature America, Inc.

The Japanese Office Action issued on Jan. 9, 2024 in a counterpart Japanese patent application No. 2020-105774, 12 pages.

Akihiro Isozaki et al: "A practical guide to intelligent image-activated cell sorting", Nature Protocols, Published online on Jul. 5, 2019, vol. 14, pp. 2370-2415.

Extended European search report issued on Nov. 10, 2021 in European patent application No. 21180003.2.

* cited by examiner

Detection unit signal
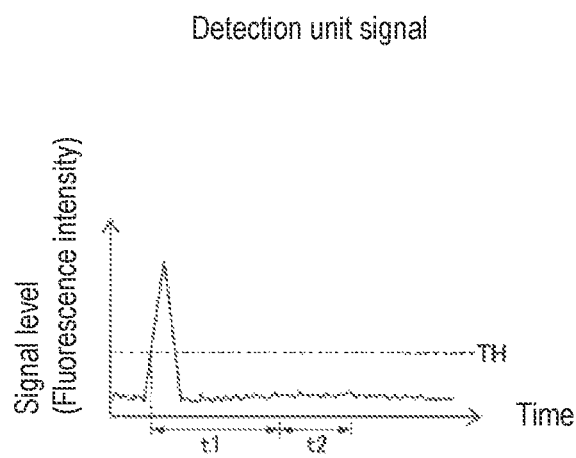
FIG. 27
FIG. 28A Fluorescence intensity < threshold TH
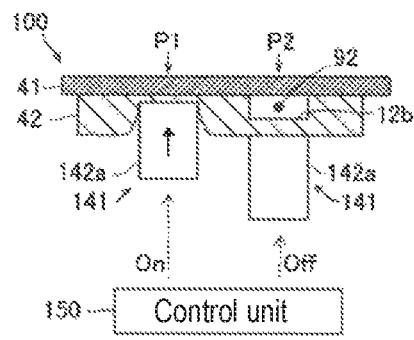
FIG. 28B Fluorescence intensity ≥ threshold TH
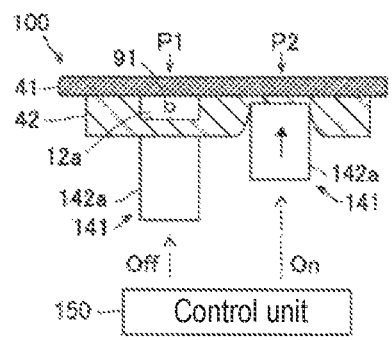
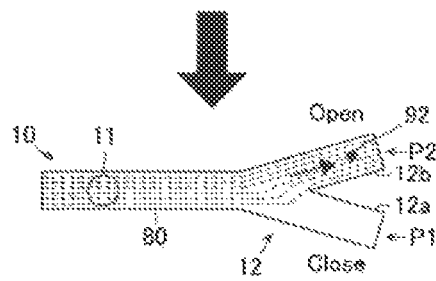

First sorting step

Second sorting step

Example

Comparative example 1

PARTICLE SORTER, PARTICLE SORTING METHOD, AND MICRO FLOW PATH CARTRIDGE

RELATED APPLICATIONS

This application claims priority to Japanese Patent Application No. 2020-105774, filed on Jun. 19, 2020, the entire content of which is incorporated herein by reference.

BACKGROUND OF THE INVENTION

1. Field of the Invention

The present invention relates to a particle sorter for separating target particles from a sample, a particle separation method, and a micro flow path cartridge.

2. Description of the Related Art

In U.S. Patent Publication No. US20180298324A1, as shown in FIG. 36, discloses a replaceable flow path cartridge 900 including a sample reservoir 901, a waste liquid reservoir 902, a sheath liquid reservoir 903, a sorting liquid reservoir 904, a recovery reservoir 905, a main flow path 906, a sheath flow path 907, and a sorting flow path 908. A sample flows from the sample reservoir 901 to the main flow path 906. The sheath liquid joins the main flow path 906 from the sheath liquid reservoir 903 through the sheath flow path 907. Specific particles flowing through the main flow path 906 are detected in the detection region 909. A sorting pulse flow from the sorting liquid reservoir 904 to the recovery reservoir 905 is generated by pulsed air pressure with a timing such that the particles determined to be the sorting target particles pass through the intersection of the main flow path 906 and the sorting flow path 908 so as to separate the target particles.

SUMMARY OF THE INVENTION

In U.S. Patent Publication No. US20180298324A1, when the sample stored in the sample reservoir 901 is sent to the waste liquid reservoir 902, the sorting target particles detected in the detection region 909 are sorted into the recovery reservoir 905. When all the samples stored in the sample reservoir 901 are sent to the waste liquid reservoir 902, the sorting process is completed. However, since the purity of the target particles by the sorting process (the ratio of the target particles to the total particles in the sample after the sorting process) and throughput (a number of processed particles in a unit time) are in trade-off relationship, it is necessary to slow down the flow velocity of the sample to sort target particles with sufficient purity, and, hence, it takes a long time to separate the particles. In particular, when target particles having an extremely low abundance are separated from a sample containing a large number of other non-target particles, it is difficult to separate the target particles with sufficient purity within a reasonable time.

The present invention provides a particle sorter, a particle sorting method, and a micro flow path cartridge that can reduce the time required to sort target particles with sufficient purity.

A particle sorter according to a first invention, shown in FIG. 1, is a particle sorter (200) including a micro flow path cartridge (100) including a first flow path (10) comprising a detection region (11) for detecting target particles contained in a sample and a sorting region (12) for obtaining a target particle-containing sample (81) containing the detected target particles, and a second flow path (20) for returning the target particle-containing sample to upstream of the detection region; an installation part (110) where the micro flow path cartridge is installed; a liquid feeder (120) configured to feed liquid in the micro flow path cartridge; a detector (130) configured to output a signal corresponding to the target particle passing through the detection region; a sorting mechanism (140) configured to perform a sorting operation for obtaining the target particle-containing sample in the sorting region based on the signal from the detector; and a controller (150) configured to control the liquid feeder such that the target particle-containing sample obtained in the sorting region is returned to upstream of the detection region via the second flow path, and control the sorting mechanism so as to perform the sorting operation on the returned target particle-containing sample.

The sorting operation can be repeated a plurality of times inside the micro flow path cartridge (100) by returning the sample using the second flow path (20) formed in the micro flow path cartridge (100). Here, the target particle-containing sample (81) obtained by the sorting operation also includes particles other than the target particles (91) flowing near the target particles (91) in the sorting region (12). Therefore, the target particles (91) can be sorted with high purity even if the sample flows at a higher speed than in the case where the sorting process is performed only once by performing the sorting operation a plurality of times. As a result, the time required to sort the target particles (91) with sufficient purity can be shortened in the overall sorting process.

A particle sorting method according to a second invention, shown in FIG. 2, is a method for sorting target particles (91) using a micro flow path cartridge (100) including a first flow path (10) comprising a detection region (11) for detecting target particles contained in a sample and a sorting region (12) for obtaining a target particle-containing sample (81) containing the detected target particles, and a second flow path (20) for returning the target particle-containing sample to upstream of the detection region, the particle sorting method comprising: obtaining (S1) the target particle-containing sample from the sample by feeding the sample to the first flow path of the micro flow path cartridge and performing a sorting operation in the sorting region based on a signal corresponding to the target particle passing through the detection region; returning (S2) the target particle-containing sample obtained by the obtaining to the first flow path via the second flow path; and feeding (S3) the returned target particle-containing sample to the detection region and the sorting region of the first flow path and performing the sorting operation based on the signal corresponding to the target particle passing through the detection region.

In the particle sorting method according to the second invention, the first sorting step (S1) and the second sorting step (S3) can be performed a plurality of times by performing the above-mentioned return step (S2). Hence, the target particles (91) can be sorted with high purity even if the sample flows at a higher speed than compared to when the sorting process is performed only once, by performing the sorting operation a plurality of times. Therefore, the time required to sort the target particles (91) with sufficient purity can be shortened similar to the first invention.

A micro flow path cartridge (100) according to a third invention, shown in FIG. 1, is the micro flow path cartridge (100) including a flow path forming body (40) in which a flow path (MC) for flowing a sample (91) containing target particles is formed; wherein the flow path comprises a first flow path (10) having a detection region (11) for detecting the target particles contained in the sample and a sorting region (12) for obtaining the detected target particles (81), and a second flow path (20) for returning the target particle-containing sample containing the target particles upstream of the detection region of the first flow path.

The micro flow path cartridge (100) according to the third invention has, as described above, a flow path (MC) which includes a second flow path (20) for returning the target particle-containing sample (81) containing the sorted target particles (91) to upstream of the detection region (11) of the first flow path (10). In this way the sorting operation can be repeated a plurality of times using the second flow path (20) similar to the first invention. Therefore, the target particles (91) can be sorted with high purity even if the sample flows at a higher speed compared to when the sorting process is performed only once, by performing the sorting operation a plurality of times. As a result, the time required to sort the target particles (91) with sufficient purity can be shortened.

According to the present invention, it is possible to provide a particle sorter, a particle sorting method, and a micro flow path cartridge that can reduce the time required to sort target particles with sufficient purity.

BRIEF DESCRIPTION OF THE DRAWINGS

FIG. 27 is a graph illustrating an output signal of a detection unit;

FIG. 28 is a diagram (A) and (B) illustrating the sorting operation control of the sorting mechanism by the control unit;

DETAILED DESCRIPTION OF THE PREFERRED EMBODIMENTS

Hereinafter, embodiments will be described with reference to the drawings.

Outline of Particle Sorter

An outline of the particle sorter according to the present embodiment will be described with reference to FIG. 1.

Figure 1:
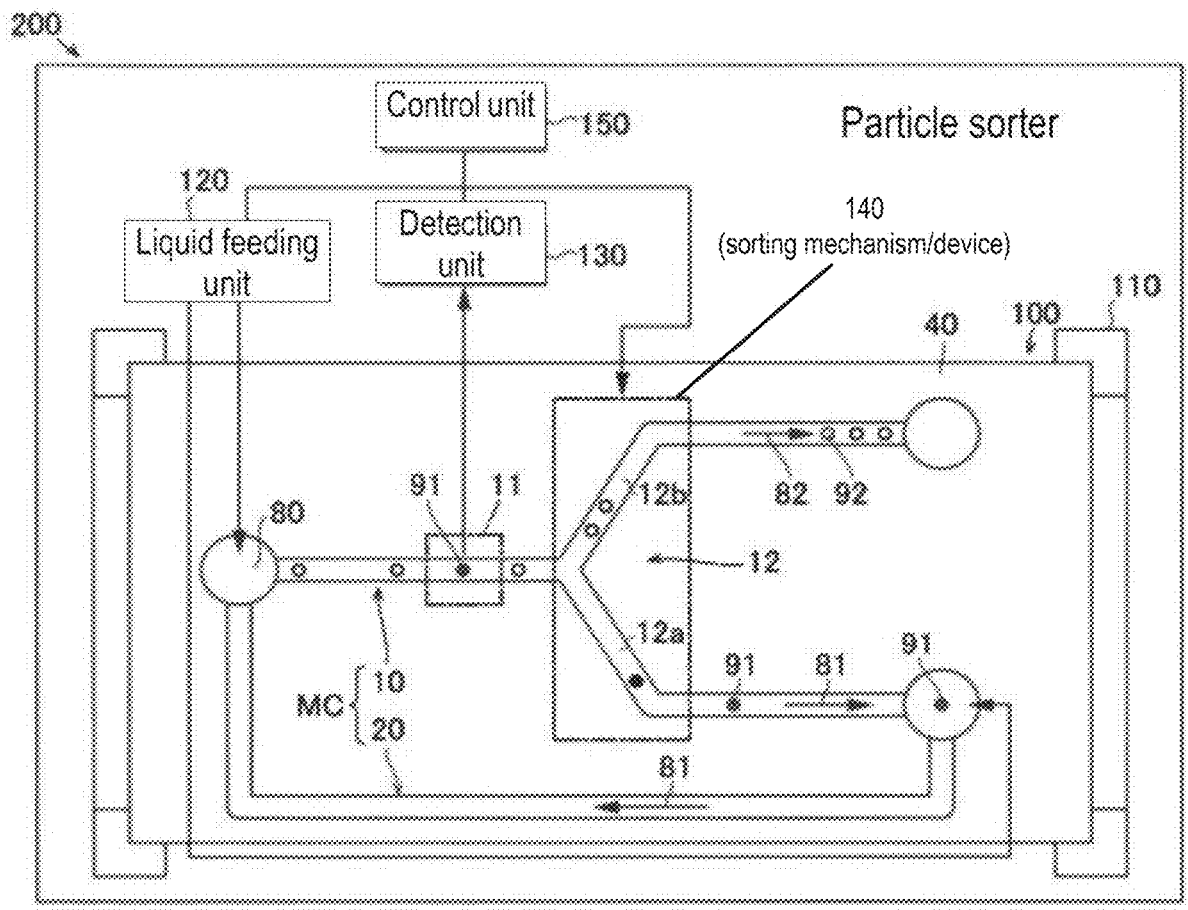
FIG. 1 is a diagram illustrating an outline of a micro flow path cartridge and a particle sorter.

As shown in FIG. 1, the particle sorter 200 is a device that uses the micro flow path cartridge 100 to perform a process of sorting target particles 91 in a sample 80 flowing in the flow path MC of the micro flow path cartridge 100.

Sorting means separating the target substance from the sample solution. Sample 80 is a liquid containing a large number of particles. The sample 80 includes a target particle 91 and a non-target particle 92 in addition to the target particle 91.

Particles are a general term for small objects, regardless of their constituent materials or structures. As used herein, particles are a broad concept that includes particulate matter of cells, macromolecules, inorganic or organic materials. Examples of the target particle 91 may be (1) cells, (2) granules such as exosomes, or (3) droplets containing a predetermined component. Examples of cells include rare cells (circulating tumor cells (CTC), circulating rare cells (CRC), endothelial cancer cells and the like, primary B cells, antibody-producing hybridoma, germ cells (sperm, egg, embryo), and each single cell in cell-cell interaction and the like. Predetermined components contained in droplets include, for example, drug molecules, viruses, nucleic acids (DNA, RNA and the like), proteins (antibodies, biomarkers, enzymes) and the like.

The particle sorter 200 performs a process of separating and recovering the target particle-containing sample 81 containing the target particles 91 from the sample 80 flowing through the flow path MC. Note that the term "sorting" as used herein does not mean that the collected sample contains only the target particles 91. The sorting process by the particle sorter 200 is to increase the ratio (purity) of the number of target particles to the total number of particles in the sample. The purity of the target particles 91 in the target particle-containing sample 81 is higher than the purity of the target particles 91 in the sample 80 before sorting. Therefore, the recovered target particle-containing sample 81 contains most of the target particles 91 and some non-target particles 92 among the sample 80 that was first introduced into the micro flow path cartridge 100. However, the number of target particles 91 in the recovered target particle-containing sample 81 is not necessarily larger than the number of non-target particles 92. For example, when the target particles 91 are rare particles having an extremely small abundance in the sample 80, the number of target particles 91 in the recovered sample may be less than the number of non-target particles 92 mixed in the recovered sample together with the target particles 91.

Particle Sorter Structure

The particle sorter 200 includes an installation unit 110, a liquid feeding unit 120, a detection unit 130, a sorting mechanism 140, and a control unit 150.

The installation unit 110 provides an installation location for the micro flow path cartridge 100. The installation unit 110 contacts a part of the micro flow path cartridge 100 and holds the micro flow path cartridge 100. The installation unit 110 supports, for example, the lower surface of the micro flow path cartridge 100.

In the present embodiment, the micro flow path cartridge 100 installed in the installation unit 110 is configured with a first flow path 10 having a detection region 11 for detecting the target particles 91 contained in the sample and a branched sorting region 12 for sorting a target particle-containing sample 81 containing the detected target particles 91, and a second flow path 20 for returning the target particle-containing sample 81 upstream of the detection region 11 of the first flow path 10. In the first flow path 10, the detection region 11 and the sorting region 12 are arranged in order from the upstream side.

The liquid feeding unit 120 is configured to feed a liquid in the micro flow path cartridge 100. The liquid feeding unit 120 can feed the sample 80 in the micro flow path cartridge 100 from the upstream to the downstream of the first flow path 10. The liquid feeding unit 120 can feed the target particle-containing sample 81 that has passed through the sorting region 12 from the upstream to the downstream of the second flow path 20. The target particle-containing sample 81 is returned to the first flow path 10 by the liquid transfer through the second flow path 20. The liquid feeding unit 120 can feed the target particle-containing sample 81 returned to the first flow path 10 from the upstream to the downstream of the first flow path 10.

The liquid feeding unit 120 feeds the liquid in the micro flow path cartridge 100 by pressure, for example. The liquid feeding unit 120 pressurizes and feeds the liquid, for example, by applying a positive pressure to the upstream side of the flow path MC. The liquid feeding unit 120 also may send the liquid in a form of suctioning the liquid by applying a negative pressure to the downstream side of the flow path MC, for example. The liquid feeding unit 120 includes, for example, a pump and a valve.

The detection unit 130 is configured to output a signal corresponding to the target particle 91 passing through the detection region 11. That is, the target particles 91 in the sample 80 flowing from the upstream to the downstream of the first flow path 10 by the liquid feeding unit 120 are detected by the detection unit 130 when passing through the detection region 11. The detection unit 130 outputs a signal reflecting the presence of the target particle 91 to the control unit 150.

The method for detecting the target particles 91 by the detection unit 130 is not particularly limited. The target particle 91 may be labeled for detection. For example, the target particle 91 can be labeled with a labeled antibody that specifically binds to the target particle 91. As the labeling method, a method according to the detection method is selected from the known labeling methods. For the detection, for example, a method such as fluorescence detection, magnetic detection, image detection, or electric detection may be adopted. In fluorescence detection, the detection unit 130 detects the target particles 91 by detecting the fluorescence generated from the fluorescent label with a photodetector. In magnetic detection, the detection unit 130 detects the target particles 91 labeled with the magnetic particles by the magnetic detector. In image detection, the detection unit 130 photographs the target particles 91 passing through the detection region 11 with an image sensor, and detects the target particles 91 by image recognition. In electric detection, the detection unit 130 detects the target particles 91 based on the change in electrical resistance and the change in impedance due to the passage of the target particles 91 between electrodes provided in the detection region 11.

The sorting mechanism 140 is configured to perform a sorting operation for sorting the target particle-containing sample 81 in the sorting region 12 based on the signal from the detection unit 130. In the sorting region 12, the first flow path 10 is branched. The number of branches is at least two. In the example of FIG. 1, the sorting region 12 is bifurcated into a first guide path 12a and a second guide path 12b. The sorting mechanism 140 causes the target particles 91 detected by the detection unit 130 in the detection region 11 to flow into one specific flow path (first guide path 12a) in the sorting region 12. When the target particles 91 contained in the sample 80 reach the sorting region 12 one after another, the sorting mechanism 140 causes the target particles 91 to flow into the same first guide path 12a. On the other hand, the sorting mechanism 140 causes the non-target particles 92 to flow into a flow path (second guide path 12b) that is different from that of the target particles 91. In this way the target particle-containing sample 81 is sorted in the sorting region 12.

The method of sorting the target particles 91 by the sorting mechanism 140 is not particularly limited. The sorting mechanism 140 may apply some external force to the target particle 91 itself or a small volume sample 80 containing the target particle 91 in the first flow path 10 for sorting. As the sorting method, for example, a laser method, a pressure method, an electric method, a magnetic method, an acoustic wave method, a flow path switching method, or the like may be employed.

In the laser method, the sorting mechanism 140 irradiates the sample 80 flowing through the sorting region 12 with laser light to generate minute bubbles to cause a pressure change, thereby pushing the target particles 91 into the first guide path 12a. In the pressure system, the sorting mechanism 140 sends the target particles 91 to the first guide path 12a by applying pressure in a direction crossing the sorting region 12. The pressure is applied from the outside of the micro flow path cartridge 100 or via an actuator provided inside the micro flow path cartridge 100. In the electric method, the sorting mechanism 140 charges the target particles 91 and sends the target particles 91 to the first guide path 12a by the principle of dielectrophoresis. In the magnetic method, the sorting mechanism 140 sends the target particles 91 to the first guide path 12a by applying a magnetic force to the target particles 91 bonded to the magnetic particles. In the acoustic wave method, the sorting mechanism unit 140 sends the target particles 91 to the first guide path 12a by applying an acoustic wave to the sorting region 12 by a transducer and forming a pressure gradient in the flow path MC. In the flow path switching method, the particles 91 are sent to the first guide path 12a and the non-target particles 92 are sent to the second guide path 12b by the sorting mechanism 140 driving a valve structure provided in the micro flow path cartridge 100 to open and close the first guide path 12a and the second guide path 12b from the outside.

The control unit 150 is configured to control the liquid feeding unit 120, the detection unit 130, and the sorting mechanism 140. The control unit 150 controls the liquid feeding unit 120 to start, stop, open/close the valve, and the like. The control unit 150 controls the detection unit 130 and acquires a signal from the detection unit 130. The control unit 150 controls the sorting operation by the sorting mechanism 140 based on the signal corresponding to the target particle 91. The control unit 150 is configured by a computer and includes one or more processors and a storage unit including volatile memory and non-volatile memory.

In the sorting operation, it is difficult to take out only the target particles 91 without mixing the non-target particles 92. Therefore, the target particle-containing sample 81 includes sorted target particles 91, and non-target particles 92 mixed with the target particles 91.

The control unit 150 controls the liquid feeding unit 120 to return the target particle-containing sample 81 sorted by the sorting mechanism 140 to upstream of the detection region 11 of the first flow path 10 via the second flow path 20, and controls the sorting mechanism 140 to perform a sorting operation on the returned target particle-containing sample 81. That is, in the present embodiment, the first sorting operation is performed on the sample 80, and the second sorting operation is performed on the target particle-containing sample 81 collected as a result of the first sorting operation. The sorting operation also may be performed three or more times. The proportion of the non-target particles 92 decreases, and the purity of the target particles 91 increases by repeating the sorting operation.

Particle Sorter Effectiveness

In the particle sorter 200 of the present embodiment described above, the control unit 150 controls the liquid feeding unit 120 to return the target particle-containing sample 81 sorted by the sorting mechanism 140 to upstream of the detection region 11 of the first flow path 10 via the second flow path 12, and controls the sorting mechanism 140 so as to perform a sorting operation on the returned target particle-containing sample 81. In this way the sorting operation can be repeated a plurality of times inside the micro flow path cartridge 100 by returning the sample using the second flow path 20 formed in the micro flow path cartridge 100. Here, the target particle-containing sample 81 obtained by the sorting operation also includes particles other than the target particles 91 flowing near the target particles 91 in the sorting region 12. Therefore, the target particles 91 can be sorted with high purity even if the sample flows at a higher speed than in the case where the sorting process is performed only once by performing the sorting operation a plurality of times. As a result, the time required to sort the target particles 91 with sufficient purity in the entire sorting process can be shortened.

Particle Sorting Method Summary

Next, the particle sorting method according to the present embodiment will be summarized. The particle sorting method of the present embodiment is a method for sorting target particles 91 using a micro flow path cartridge 100 including a first flow path 10 having a detection region 11 for detecting the target particles 91 contained in the sample and a branched sorting region 12 for sorting the detected target particles 91, and a second flow path 20 for returning the target particle-containing sample 81 containing the sorted target particles 91 to upstream of the detection region 11 of the first flow path 10. The particle sorter 200 described above is a device that implements the particle sorting method according to the present embodiment by controlling the liquid feeding unit 120, the detecting unit 130, and the sorting mechanism 140 via the control unit 150.

Figure 2:
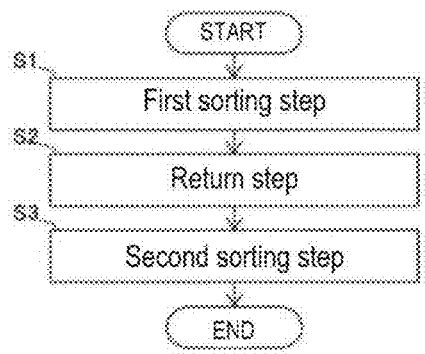
FIG. 2 is a flow chart showing a particle sorting method.

As shown in FIG. 2, the particle sorting method includes at least a first sorting step S1, a return step S2, and a second sorting step S3.

The first sorting step S1 includes sending the sample 80 to the first flow path 10 of the micro flow path cartridge 100 and sorting the target particle-containing sample 81 from the sample 80 based on the signal corresponding to the target particles 91 passing through the detection region 11. In the case of the structural example of FIG. 1, the control unit 150 controls the liquid feeding unit 120 to feed the sample 80 from the upstream to the downstream of the first flow path 10. The detection unit 130 outputs a signal corresponding to the target particle 91 that has reached the detection region 11. The control unit 150 controls the sorting mechanism 140 so as to send the target particle-containing sample 81 that has reached the sorting region 12 to the first guide path 12a based on the signal from the detection unit 130. The control unit 150 controls the sorting mechanism 140 so as to send the sample that does not contain the target particles 91 that has reached the sorting region 12 to the second guide path 12b.

The return step S2 includes returning the target particle-containing sample 81 sorted by the first sorting step to the first flow path 10 via the second flow path 20. In the case of the structural example of FIG. 1, after the first sorting step S1, the control unit 150 controls the liquid feeding unit 120 to send the target particle-containing sample 81 delivered to the first guide path 12a from the upstream to the downstream of the second flow path 20. In this way the target particle-containing sample 81 is returned upstream from the detection region 11 of the first flow path 10.

The second sorting step S3 includes sending the returned target particle-containing sample 81 to the detection region 11 and the sorting region 12 and performing a sorting operation based on the signals corresponding to the target particles 91 passing through the detection region 11. In the case of the structural example of FIG. 1, after the return step S2, the control unit 150 controls the liquid feeding unit 120 to send the target particle-containing sample 81 from the upstream to the downstream of the first flow path 10. The detection unit 130 outputs a signal corresponding to the target particle 91 that has reached the detection region 11. The control unit 150 controls the sorting mechanism 140 so as to send the target particle-containing sample 81 that has reached the sorting region 12 to the first guide path 12a based on the signal from the detection unit 130. The control unit 150 controls the sorting mechanism 140 so as to send the sample that does not contain the target particles 91 that has reached the sorting region 12 to the second guide path 12b. The return step S2 and the second sorting step S3 may be further repeated.

In the particle sorting method according to the present embodiment, by performing the above-mentioned return step S2, the first sorting step S1 and the second sorting step S3 can be repeated a plurality of times. Hence, the target particles 91 can be sorted with high purity even if the sample flows at a higher speed than compared to when the sorting process is performed only once, by performing the sorting operation a plurality of times. Therefore, the time required to sort the target particles 91 with sufficient purity can be shortened.

Micro Flow Path Cartridge Summary

The micro flow path cartridge according to the present embodiment will be summarized with reference to FIG. 1.

The micro flow path cartridge 100 includes a flow path MC. The flow path MC is a tubular element through which a fluid can flow. The micro flow path cartridge 100 can sort the target particles 91 from the sample 80 containing a plurality of types of particles in the flow path MC.

The micro flow path cartridge 100 includes a flow path forming body 40 in which the flow path MC for flowing a sample containing the target particles 91 is formed. The flow path forming body 40 is installed in the installation unit 110 of the particle sorter 200.

Examples of the material of the flow path forming body 40 include glass, silicon, polydimethylsiloxane (PDMS), polymethylmethacrylate resin (PMMA), cyclic olefin resin (COC), cycloolefin polymer resin (COP), polyethylene terephthalate (PET), polycarbonate (PC), polytetrafluoroethylene (PTFE), metals and the like.

In the present embodiment, the flow path MC includes a first flow path 10 and a second flow path 20.

The first flow path 10 has a detection region 11 for detecting the target particles 91 contained in the sample and a branched sorting region 12 for sorting the detected target particles 91.

The detection region 11 is a part of the first flow path 10, and is located between the upstream end and the downstream end of the first flow path 10. The detection region 11 is arranged upstream of the sorting region 12. The detection region 11 is configured so that the target particles 91 can be externally detected by the detection unit 130 of the particle sorter 200. For example, when optical detection is performed, the detection region 11 has translucency and the target particles 91 in the flow path MC can be detected from outside the flow path MC.

The sorting region 12 is a part of the first flow path 10, and is located between the upstream end and the downstream end of the first flow path 10. The sorting region 12 is arranged downstream of the detection region 11. The sorting region 12 is connected to the detection region 11 on the upstream side. The downstream side of the sorting region 12 branches into at least two flow paths. In FIG. 1, the sorting region 12 includes a first guide path 12a and a second guide path 12b extending downstream, respectively. The first guide path 12a and the second guide path 12b are connected to each other at the upstream end to form a branched path. The first guide path 12a directly or indirectly communicates with the second flow path 20. The first guide path 12a is a flow path through which the target particle-containing sample 81 flows. The second guide path 12b is not connected to the second flow path 20. The second guide path 12b is a flow path through which the non-target particles 92 flow.

The second flow path 20 is provided to return the target particle-containing sample 81 containing the sorted target particles 91 to the upstream side of the detection region 11 of the first flow path 10. The liquid feeding direction in the second flow path 20 (from right to left in FIG. 1) is opposite to the liquid feeding direction in the first flow path 10 (from left to right in FIG. 1). The target particle-containing sample 81 containing the separated target particles 91 is sent to the upstream end of the second flow path 20. The upstream side of the second flow path 20 directly or indirectly communicates with the first guide path 12a. The downstream side of the second flow path 20 is directly or indirectly connected to the first flow path 10.

The return position of the target particle-containing sample 81 from the second flow path 20 to the first flow path 10 is at least upstream of the detection region 11. In this way the target particle-containing sample 81 returned to the first flow path 10 is flowed again toward the downstream of the first flow path 10, so that the target particles 91 can be detected in the detection region 11 and a sorting operation can be performed in the sorting region 12 based on the signal from the detection unit 130.

The micro flow path cartridge 100 may also be provided with a valve structure for opening and closing the flow path MC in order to supply the liquid from the upstream to the downstream of the first flow path 10 and the liquid from the upstream to the downstream of the second flow path 20. For example, one valve structure is provided in each of the first guide path 12a, the second guide path 12b, and the second flow path 20. The valve structure may be an on/off valve that opens and closes (that is, communicates and shuts off) the flow path MC, or a check valve that prevents a flow (backflow) from downstream to upstream. As will be described later, the flow path MC also may be opened and closed by applying a pressing force from the outside to the portion of the flow path MC of the micro flow path cartridge 100 to deform the pressing portion. Therefore, the micro flow path cartridge 100 does not have to be provided with a valve structure.

The micro flow path cartridge 100 according to the present embodiment includes the second flow path 20 so that the flow path MC returns the target particle-containing sample 81 containing the sorted target particles 91 upstream of the detection region 11 of the first flow path 10. In this way he sorting operation can be repeated a plurality of times using the second flow path 20. By performing the sorting operation a plurality of times, the target particles 91 can be sorted with high purity even if the sample flows at a higher speed than in the case where the sorting process is performed only once. As a result, the time required to sort the target particles 91 with sufficient purity can be shortened.

Micro Flow Path Cartridge Structural Example

Next, the structure of the micro flow path cartridge 100 will be illustrated. The micro flow path cartridge 100 also may include a liquid reservoir for accommodating a liquid such as a sample 80 or a target particle-containing sample 81. The liquid reservoir can be, for example, a chamber, reservoir, well and the like.

Figure 3:
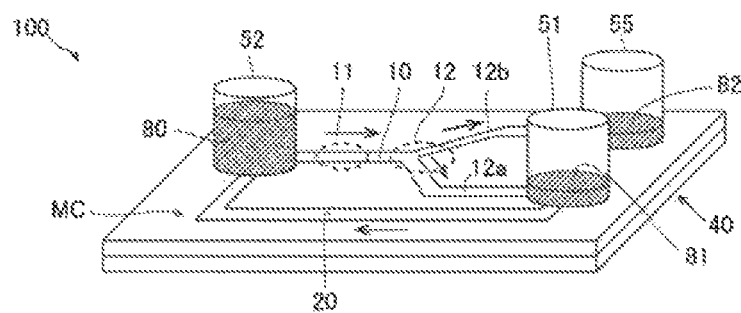
FIG. 3 is a perspective view showing a structural example of a micro flow path cartridge.

In the example shown in FIG. 3, the flow path forming body 40 has a flat plate shape, and a tubular chamber is provided so as to rise from the main surface of the flat plate-shaped flow path forming body 40.

As shown in FIG. 3, the flow path forming body 40 is configured with a recovery chamber 51 for collecting the target particle-containing sample 81 sorted in the sorting region 12 of the first flow path 10. The recovery chamber 51 is connected to the downstream end of the first guide path 12a, which is one of the branched sorting regions 12. The target particle-containing sample 81 sent to the first guide path 12a is housed in the recovery chamber 51. In this way the sorted target particle-containing sample 81 can be housed in the recovery chamber 51 and then sent to the second flow path 20 without being discharged to the outside. Since the target particle-containing sample 81 can be returned without being taken out to the outside, the sampling process can be performed without the risk of contamination even if the sampling operation is performed a plurality of times.

In the example of FIG. 3, the upstream end of the second flow path 20 communicates with the recovery chamber 51. In this way the target particle-containing sample 81 can be directly sent from the recovery chamber 51 to the second flow path 20. For example, it is possible to prevent the target particles 91 from remaining in the liquid feeding path because since the liquid feeding path of the target particle-containing sample 81 does not become unnecessarily long, compared to when all of the target particle-containing sample 81 is accommodated in the second flow path 20.

In the example of FIG. 3, the micro flow path cartridge 100 is formed with a sample chamber 52 for storing the sample 80 to be fed to the first flow path 10. In this way the sample 80 previously injected and stored in the sample chamber 52 is supplied into the first flow path 10 by the liquid feeding unit 120 instead of supplying the sample 80 from the liquid feeding unit 120. The downstream end of the second flow path 20 communicates with the sample chamber 52.

Figure 4:
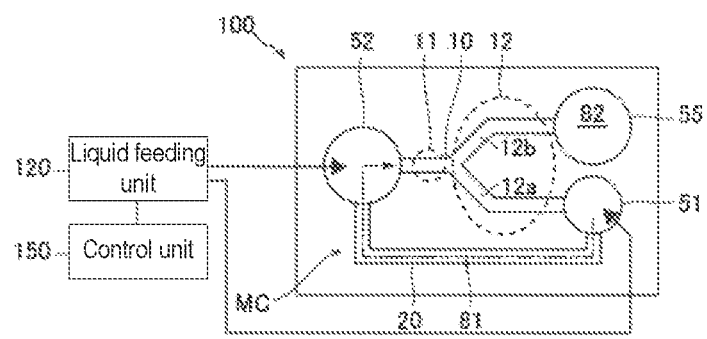
FIG. 4 is a schematic view showing an example of returning a target particle-containing sample from the second flow path to a sample chamber.

In this case, as shown in FIG. 4, the control unit 150 controls the liquid feeding unit 120 so as to sort the target particle-containing sample 81 from the sample 80 (see FIG. 3) fed to the first flow path 10 from the sample chamber 52, and so that the sorted target particle-containing sample 81 is returned to the first flow path 10 via the second flow path 20 and the sample chamber 52. In this way the sorted target particle-containing sample 81 can be housed in the sample chamber 52 that housed the original sample 80. That is, the liquid feeding of the original sample 80 in the first sorting operation and the liquid feeding of the target particle-containing sample 81 in the second and subsequent sorting operations can be performed with the same structure. Therefore, the structure and control of the particle sorter 200 can be simplified as compared with the case where the original sample 80 and the target particle-containing sample 81 are housed in separate chambers.

In the examples of FIGS. 3 and 4, the micro flow path cartridge 100 is formed with a waste chamber 55 for storing the sample 82 that has not been sorted as the target particle-containing sample 81 in the sorting region 12. The waste chamber 55 is connected to the downstream end of the second guide path 12b, which is the other end of the branched sorting region 12. The sample 80 sent to the second sorting 12b is housed in the waste chamber 55. In this way the sorting operation can be repeated a plurality of times without discharging the unsorted sample 82 to the outside. In particular, when the micro flow path cartridge 100 provided with the sample chamber 52, the recovery chamber 51, and the waste chamber 55 is made disposable, the particle sorter 200 does not come into contact with the sample, and a series of operations from injection of the sample 80 to multiple sorting and disposal can be completed in the micro flow path cartridge 100.

Figure 5:
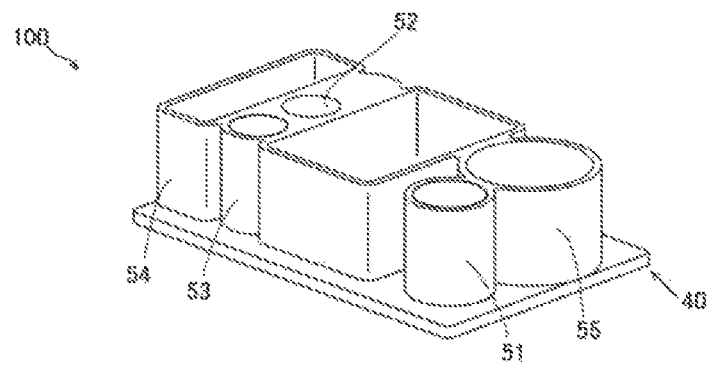
FIG. 5 is a perspective view showing a structural example of a micro flow path cartridge provided with a reservoir.
Figure 6:
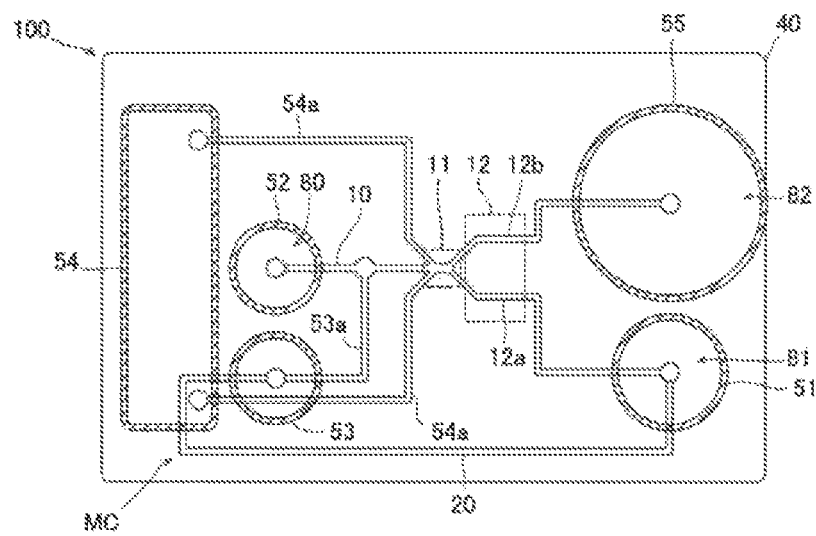
FIG. 6 is a schematic plan view of FIG. 5.

In the examples shown in FIGS. 5 and 6, the flow path forming body 40 includes a sample chamber 52 for storing a sample to be fed to the first flow path 10, a reservoir 53 that communicates with the downstream end of the second flow path 20 (see FIG. 6), and a connecting flow path 53a connected to the first flow path 10 upstream of the detection region 11. The reservoir 53 is provided separately from the sample chamber 52.

Figure 7:
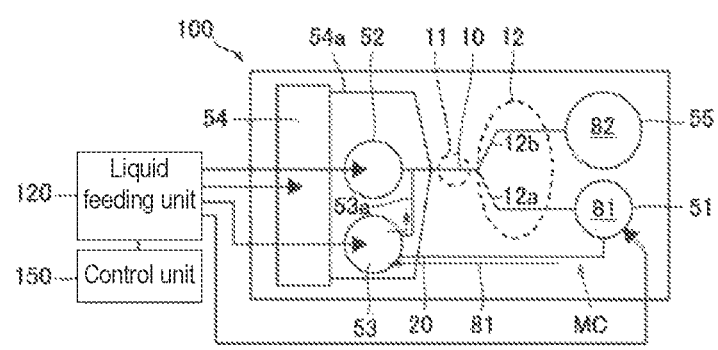
FIG. 7 is a schematic diagram illustrating the return of a target particle-containing sample via a reservoir.

In this case, the control unit 150 controls sorting mechanism 140 to sort the target particle-containing sample 81 from the sample 80 (see FIG. 6) sent from the sample chamber 52 to the first flow path 10 (see FIG. 1) and, as shown in FIG. 7, controls the liquid feeding unit 120 to return the sorted target particle-containing sample 81 to the first flow path 10 via the second flow path 20, the reservoir 53, and the connecting flow path 53a. That is, in the first sorting step, the sample 80 is sent from the sample chamber 52 to the first flow path 10. The sorted target particle-containing sample 81 is accommodated in the reservoir 53 via the recovery chamber 51 and the second flow path 20. In the second sorting step, the target particle-containing sample 81 is sent from the reservoir 53 to the first flow path 10 via the connecting flow path 53a.

In this way it is possible to prevent residual particles in the sample chamber 52 from being mixed into the target particle-containing sample 81 by accommodating the target particle-containing sample 81 in the reservoir 53 separate from the sample chamber 52. Therefore, the purity of the target particles 91 in the target particle-containing sample 81 can be increased as compared with the case where the target particle-containing sample 81 is returned to the sample chamber 52.

In the examples shown in FIGS. 6 and 7, the flow path forming body 40 includes a sheath liquid chamber 54 for storing sheath liquid and communicates with the sheath liquid chamber 54, and a sheath liquid flow path 54a connected upstream of the detection region 11 of the first flow path 10, that is, downstream of the confluence point with the connecting flow path 53a of the first flow path 10. In the sorting operation, the control unit 150 controls the liquid feeding unit 120 to send the sample 80 or the target particle-containing sample 81 to the first flow path 10, and send the sheath liquid from the sheath liquid chamber 54 to the first flow path via the sheath liquid flow path 54a. As a result, the sample flow is surrounded by the sheath liquid flow at the position of the detection region 11 of the first flow path 10.

In this way the particles in the sample can be aligned by the flow of the sheath liquid, so that the target particles 91 in the detection region 11 can be detected easily and with high accuracy. Then, since the sheath liquid flow path 54a is connected downstream from the confluence of the first flow path 10 and the connecting flow path 53a, the target particles can be aligned by the sheath liquid flow even when a sorting operation is performed on the target particle-containing sample 81 returned via the second flow path 20.

Here, the liquid amount of the target particle-containing sample 81 sent to the recovery chamber 51 by the first sorting step is smaller than the liquid amount of the initial sample 80 by the amount of the sample 82 sent to the waste chamber 55. For the second sorting step, the sorted target particle-containing sample 81 may be diluted.

In FIG. 7, the control unit 150 is configured to control the liquid feeding unit 120 so as to dilute the target particle-containing sample 81, and control the sorting mechanism 140 to perform a sorting operation with respect to the diluted target particle-containing sample 81.

In this way the liquid volume of the target particle-containing sample 81 can be increased by dilution, so that stable flow velocity control is possible even in the second and subsequent sorting operations. As a result, variations in sorting performance can be reduced.

Figure 8:
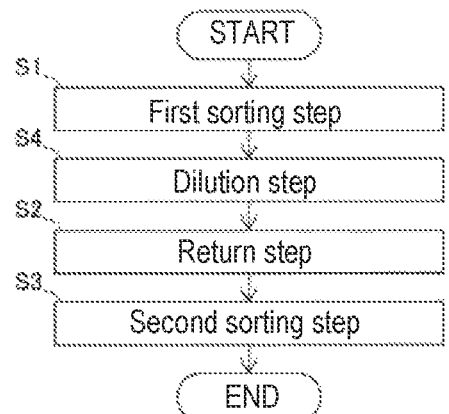
FIG. 8 is a flow chart showing an example of a particle sorting method including a dilution step.

In this case, as shown in FIG. 8, the control unit 150 controls the liquid feeding unit 120, detection unit 130, and sorting mechanism 140 to perform a dilution step S4 for diluting the target particle-containing sample 81 between the first sorting step S1 and the second sorting step S3. That is, in FIG. 8, the particle sorting method of the present embodiment further includes a dilution step S4 for diluting the target particle-containing sample 81 between the first sorting step S1 and the second sorting step S3. The dilution step S4 may be performed before the return step S2 or after the return step S2.

Figure 9:
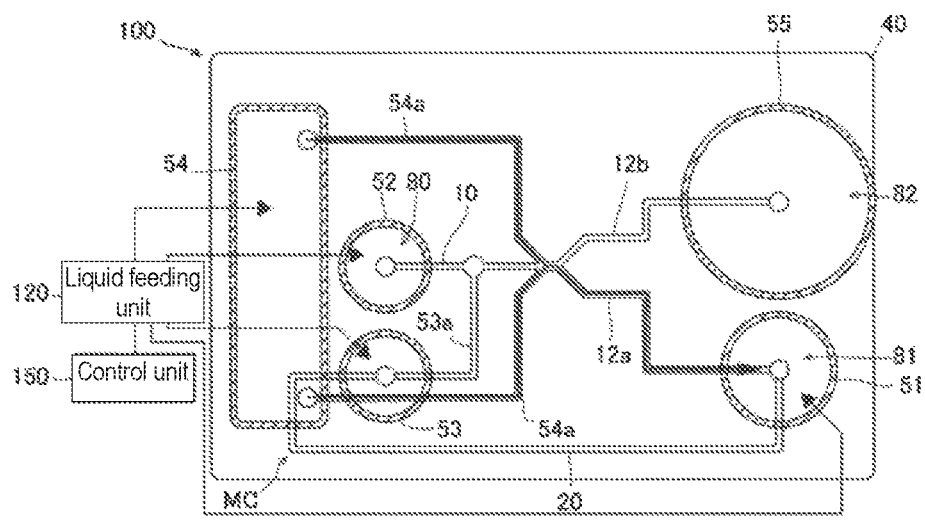
FIG. 9 is a schematic diagram describing a first example of a dilution step.

Specifically, in the example of FIG. 9, the control unit 150 controls the liquid feeding unit 120 so as to dilute the target particle-containing sample 81 in the recovery chamber 51. That is, after the first sorting step, the control unit 150 controls the liquid feeding unit 120 to send a predetermined amount of sheath liquid from the sheath liquid chamber 54 to the recovery chamber 51 via the sheath liquid flow path 54a, the first flow path 10, and the first guide path 12a. In this way uniform dilution is more easily accomplished, for example, compared to when diluting in the second flow path 20.

Figure 10:
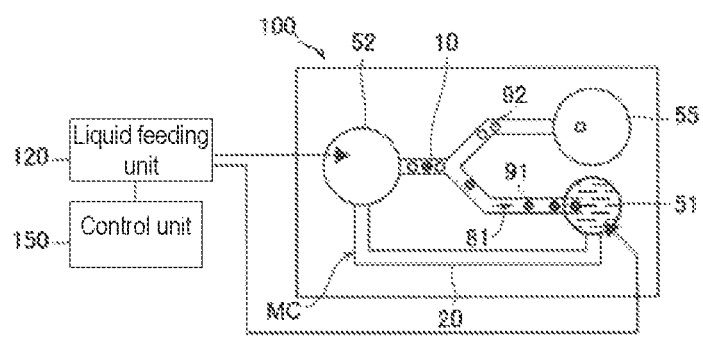
FIG. 10 is a schematic diagram for describing a second example of the dilution step.

In the example of FIG. 10, the sheath liquid for dilution is stored in the recovery chamber 51 in advance before the first sorting step. The control unit 150 controls the liquid feeding unit 120 to dilute the target particle-containing sample 81 in the recovery chamber 51 by sending the target particle-containing sample 81 to the recovery chamber 51 that stores the diluting liquid.

In this way the target particle-containing sample 81 can be easily diluted simply by sending the sorted target particle-containing sample 81 to the recovery chamber 51. Since it is not necessary to transfer the dilution liquid between the sorting operation and the return operation of the target particle-containing sample 81 by the second flow path 20, the diluted target particles can be immediately sent after the initial sorting operation.

Note that the dilution liquid may be injected into the recovery chamber 51 by the user in advance when the micro flow path cartridge 100 is installed in the installation unit 110, or a step can be performed to send the dilution liquid from the sheath liquid chamber 54 (refer to FIG. 9) to the recovery chamber 51 before the first sorting step.

As another example, after the return step S2, the control unit 150 also may control the liquid feeding unit 120 to send the dilution liquid from the sheath liquid chamber 54 to the reservoir 53 in FIG. 6, to dilute the target particle-containing sample 81 stored in the reservoir 53.

In the first and second sorting steps, it is not easy to sort all the target particles 91 flowing through the first flow path 10 into the first guide path 12a, and some of the target particles 91 cannot be sorted and are sent to the second guide path 12b. Therefore, the sample 82 sent to the second guide path 12b may be returned to the upstream of the first flow path 10.

Figure 11:
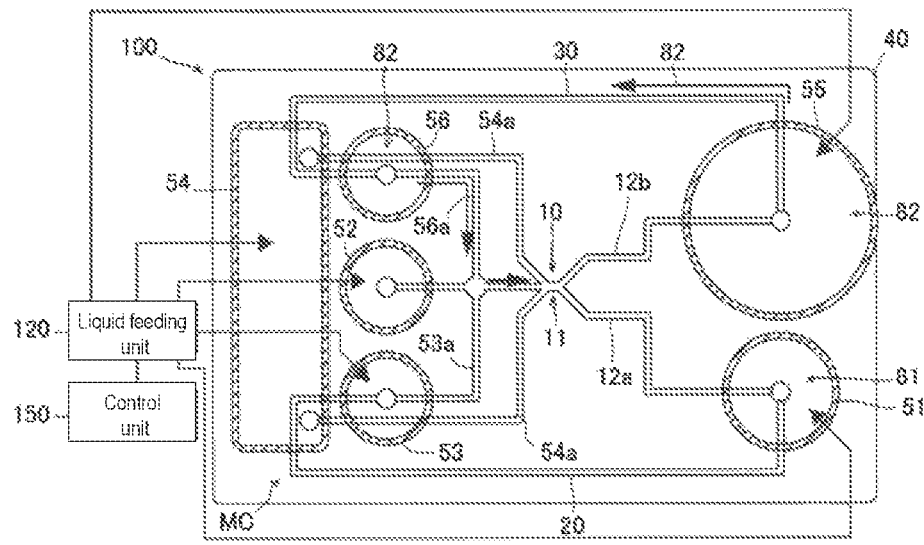
FIG. 11 is a schematic plan view showing a micro flow path cartridge provided with a third flow path.

That is, in the example of FIG. 11, the flow path forming body 40 is provided with a third flow path 30 configured to return the sample that was not sorted as the target particle-containing sample 81 in the sorting region 12 of the first flow path 10 to the upstream of the detection region 11 of the first flow path 10.

The control unit 150 controls the liquid feeding unit 120 to return the sample 82 that was not sorted as the target particle-containing sample 81 in the sorting region 12 of the first flow path 10 to the upstream of the detection region 11 of the first flow path 10 to send the returned sample 82 to the detection region 11 of the first flow path 10, and controls the sorting mechanism 140 (refer to FIG. 1) to perform a sorting operation based on the signal from the detection unit 130 (refer to FIG. 1).

In this way not only the sorting operation for the target particle-containing sample 81 but also the sorting operation for the unsorted sample 82 can be performed to recover the target particles 91 returned from the third flow path 30 due to the sorting leakage. As a result, the recovery rate of the target particles 91 in the sample 80 can be improved.

In FIG. 11, the upstream end of the third flow path 30 is connected to the waste chamber 55. The flow path forming body 40 is provided with, in addition to the third flow path 30, a second reservoir 56 communicating with the downstream end of the third flow path 30, and a connection flow path 56a connecting the upstream of the detection region 11 of the first flow path 10 and the second reservoir 56. Instead of providing the second reservoir 56 and the connection flow path 56a, the downstream end of the third flow path 30 may be connected to the sample chamber 52 or the reservoir 53, or the downstream end of the third flow path 30 may be connected upstream of the detection region 11 of the first flow path 10.

Flow Path Forming Body Structure

Next, a structural example of the flow path forming body 40 will be shown.

Figure 12:
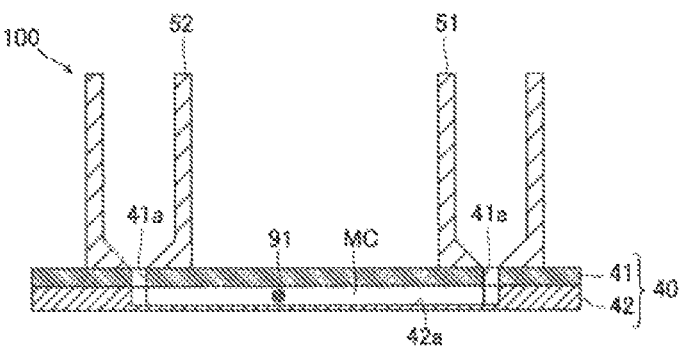
FIG. 12 is a schematic vertical cross-section view showing the structure of a flow path forming body.
Figure 13:
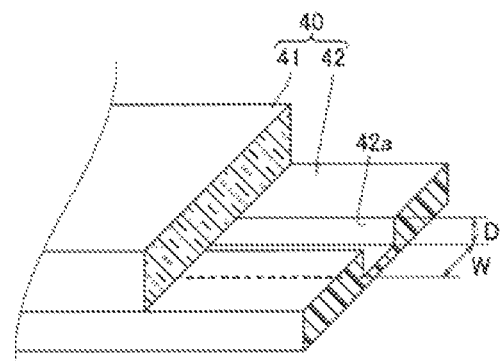
FIG. 13 is a perspective view showing a substrate and a sheet of a flow path forming body.

As shown in FIG. 12, the flow path forming body 40 includes a plate-shaped substrate 41 and a sheet 42 bonded to the substrate 41. The flow path MC is formed by grooves formed on at least one of the sheet 42 side surface of the substrate 41 and the substrate 41 side surface of the sheet 42. In the example of FIG. 13, a groove 42a is formed on the surface of the sheet 42 on the substrate 41 side, and the groove 42a is covered by the surface of the sheet 42 on the sheet 42 side to form a flow path MC having a tubular structure capable of flowing a liquid. In this way the flow path forming body 40 can be configured with a simple structure in which the sheet 42 is simply attached to the substrate 41.

The first flow path 10 and the second flow path 20 have, for example, a depth D of 1 μm or more and 1000 μm or less, and a width W of 1 μm or more and 1000 μm or less. The particle sorter 200 of the present embodiment is particularly suitable for a micro flow path cartridge 100 having such a micro flow path.

In the case of FIG. 12, liquid reservoirs such as the sample chamber 52, the recovery chamber 51, the sheath liquid chamber 54, and the reservoir 53 are formed on the main surface of the substrate 41 opposite to the sheet 42. The substrate 41 is formed with through holes 41a that penetrate the substrate 41 in the thickness direction from the main surface to the surface on the sheet 42 side. The through hole 41a connects the inner bottom portion of the liquid reservoir such as the sample chamber 52, the recovery chamber 51, the sheath liquid chamber 54, and the reservoir 53 with the flow path MC (groove portion 42a of the sheet 42). In this way the liquid inside the liquid reservoir is allowed to flow through the through hole 41a to the flow path MC by applying pressure to the upper surface opening side of the liquid reservoir such as the sample chamber 52, the recovery chamber 51, the sheath liquid chamber 54, and the reservoir 53.

Figure 14:
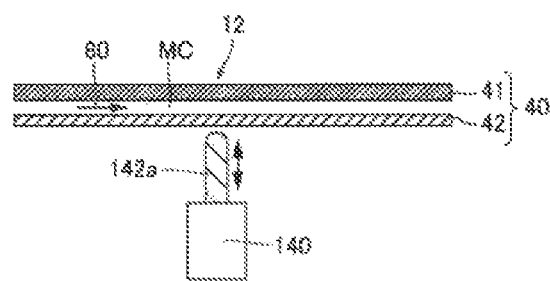
FIG. 14 is a schematic view showing an example of opening and closing a flow path by pressing a sheet.

In the example shown in FIG. 14, the sheet 42 is made of a material that is more flexible than the substrate 41 and can be elastically deformed by pressing. For example, the substrate 41 is a glass substrate and the sheet 42 is a PDMS sheet. The sorting region 12 of the first flow path 10 is configured so that the flow path MC can be blocked by pressing the sheet 42 from the outside. In the example of FIG. 13, the sorting mechanism unit 140 has a pressing part 142a that can move in the direction of approaching and separating from the sheet 42. The sheet 42 is pressed by the pressing part 142a.

In this way the flow path can be easily opened and closed simply by applying a pressing force from the outside to the sheet 42 that covers the flow path portion of the sorting region 12. Then, the target particles 91 that have reached the sorting region 12 can be easily sorted by opening and closing the flow path.

Sorting Mechanism Structure

Next, the structure of the sorting mechanism 140 will be described.

Figure 15:
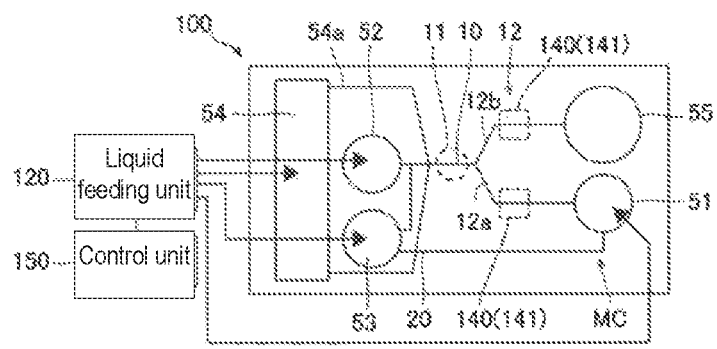
FIG. 15 is a schematic diagram describing a sorting mechanism.

In the example shown in FIG. 15, the sorting mechanism 140 includes a flow path opening/closing unit 141 that opens and closes at least one of the branched flow paths in the sorting region 12 of the first flow path 10. In this way the sorting mechanism 140 can be constructed with a compact configuration in which the flow path opening/closing unit 141 is provided, so that the structure of the particle sorter 200 can be simplified.

In the example of FIG. 15, the sorting region 12 of the first flow path 10 is bifurcated into a first guide path 12a that guides the sample to the collection chamber 51 and a second guide path 12b that is different from the first guide path. The flow path opening/closing unit 141 is provided one by one in the first guide path 12a and the second guide path 12b.

The control unit 150 is configured to control the sorting mechanism 140 so as to distribute the sample 80 and the target particle-containing sample 81 sent to the sorting region 12 to the first guide path 12a based on the signal from the detection unit 130 (see FIG. 1).

In this way the sorting mechanism 140 is configured by a flow path switching mechanism that distributes the flow of the sample to either the first guide path 12a or the second guide path 12b. Since the sorting operation can be performed by just switching the flow path, the configuration of the sorting mechanism 140 can be simplified.

The flow path opening/closing unit 141 is a pinch valve. The flow path opening/closing unit 141 is configured to close at least one of the branched flow paths by deforming the region in which at least one of the branched flow paths of the micro flow path cartridge 100 is formed by pressing from the outside.

In this way the flow path opening/closing unit 141 can be configured with a simple structure of simply pressing the micro flow path cartridge 100 from the outside. Since the flow path opening/closing unit 141 does not come into contact with the liquid inside the micro flow path cartridge 100, contamination can be prevented.

FIGS. 16 to 22 show a structural example of the flow path opening/closing unit 141. In FIGS. 16 to 22, the sheet 42, which is the lower surface of the flow path forming body 40, is shown upside down so as to be located on the upper side in the drawing.

Figure 16:
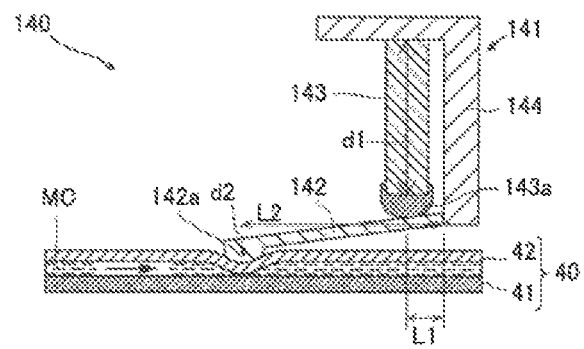
FIG. 16 is a schematic view showing a flow path opening/closing unit by a displacement-enhancing type piezoelectric actuator.

In the example shown in FIG. 16, the flow path opening/closing unit 141 includes a displacement-enhancing type piezoelectric actuator. In this way the flow path MC can be opened and closed at high speed by the highly responsive piezoelectric actuator, so that it is possible to prevent particles other than the target particles 91 from being mixed into the sorted sample. On the other hand, the piezoelectric actuator has a drawback in that the amount of displacement that can be generated is small, but since the amount of displacement can be increased by the displacement-enhancing type piezoelectric actuator, the flow path MC can be opened and closed reliably even when the flow path MC of the micro flow path cartridge 100 is pressed from the outside.

The displacement-enhancing type piezoelectric actuator includes a movable member 142 having a pressing portion 142a facing the pressing position of the micro flow path cartridge 100, a piezoelectric element 143 that moves the movable member 142, and a fixing member 144 which holds the piezoelectric element 143 and the movable member 142. The movable member 142 is configured to displace the pressing portion 142a by a displacement amount larger than the displacement amount of the piezoelectric element 143.

In this way the displacement amount of the pressing portion 142a required to reliably open and close the flow path MC of the micro flow path cartridge 100 can be easily obtained by expanding the displacement of the piezoelectric element 143 via the movable member 142.

In the example shown in FIG. 16, one end of the piezoelectric element 143 extending vertically is fixed to the fixing member 144. At the other end of the piezoelectric element 143 is provided a contact member 143a that comes into contact with the movable member 142. The piezoelectric element 143 is a so-called stack type piezoelectric actuator in which a plurality of piezoelectric bodies are laminated in the displacement generation direction. The piezoelectric element 143 expands and contracts in the vertical direction, which is the stacking direction, when a voltage is applied. The movable member 142 is arranged on the other end side of the piezoelectric element 143 so as to come into contact with the contact member 143a. The movable member 142 has a cantilever structure extending from the fixing member 144 along the sheet 42 of the flow path forming body 40. The movable member 142 has a straight plate-like shape. A pressing portion 142a is provided at the tip of the movable member 142 in a convex shape toward the sheet 42. The contact member 143a is arranged so as to come into contact with the movable member 142 at a position between the fixed end of the movable member 142 and the pressing portion 142a. In this way the displacement of the piezoelectric element 143 is expanded by the ratio of the length L1 from the fixed end to the contact member 143a and the length L2 from the fixed end to the pressing portion 142a. That is, the relationship of $d2=d1\times(L2/L1)$ is established between the displacement d1 of the piezoelectric element 143 and the displacement d2 of the pressing portion 142a. Note that $L1<L2$.

Figure 17:
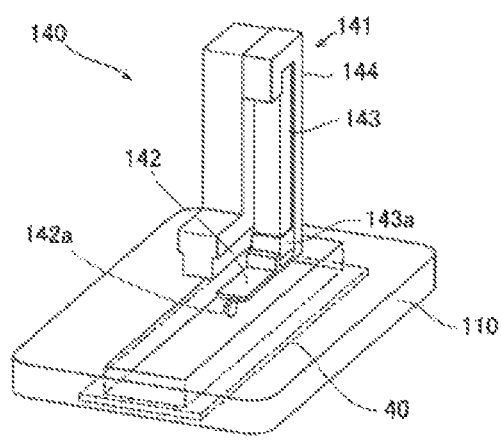
FIG. 17 is a perspective view of the flow path opening/closing unit of FIG. 16.

As shown in FIG. 17, the fixing member 144 is provided on the lower surface (upper surface in FIG. 17) of the installation unit 110. The pressing portion 142a closes the flow path MC by pushing up from beneath the sheet 42, which is the lower surface of the flow path forming body 40 exposed from the opening of the installation unit 110.

Figure 18:
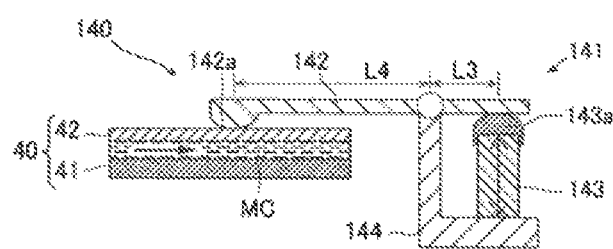
FIG. 18 is a schematic view showing another example of a displacement-enhancing type piezoelectric actuator.

In the example shown in FIG. 18, a pressing portion 142a is formed at one end of the movable member 142, and the contact member 143a of the piezoelectric element 143 is arranged at the other end of the movable member 142. Then, the fixing member 144 rotatably holds the movable member 142 at a position between the pressing portion 142a and the contact member 143a. When the piezoelectric element 143 pushes up the other end of the movable member 142, the movable member 142 rotates around the holding position via the fixing member 144 as a fulcrum, and the pressing portion 142a is displaced toward the sheet 42. In this case, the displacement of the piezoelectric element 143 is increased only by a ratio (L3/L4) of the length L3 from the contact member 143a to the holding position (fulcrum) and the length L4 from the holding position (fulcrum) to the pressing portion 142a. Note that L3<L4.

Figure 19:
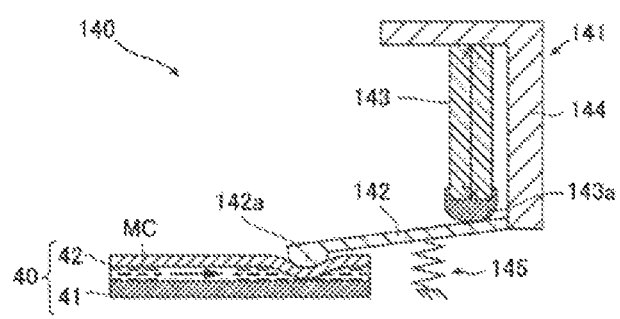
FIG. 19 is a schematic view showing a modified example of the displacement-enhancing type piezoelectric actuator of FIG. 16.
Figure 20:
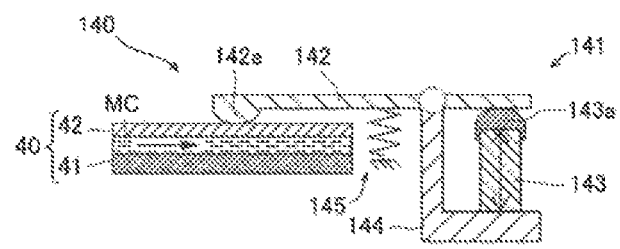
FIG. 20 is a schematic view showing a modified example of the displacement-enhancing type piezoelectric actuator of FIG. 18.

As shown in FIGS. 19 and 20, the piezoelectric actuator also may be provided with an energizing member 145 that energizes the movable member 142 in the direction in which the pressing portion 142a releases the pressing. When the flow path MC is opened again after the flow path MC is closed by the energizing member 145, the pressing portion 142a can be returned to the original position, so that the flow path MC can be reliably opened.

Other Examples of Displacement-Enhancing Piezoelectric Actuators

There are various types of displacement-enhancing piezoelectric actuator structures, and the structure is not limited to a specific structure. In the following, variations of the displacement-enhancing type piezoelectric actuator will be illustrated.

Figure 21:
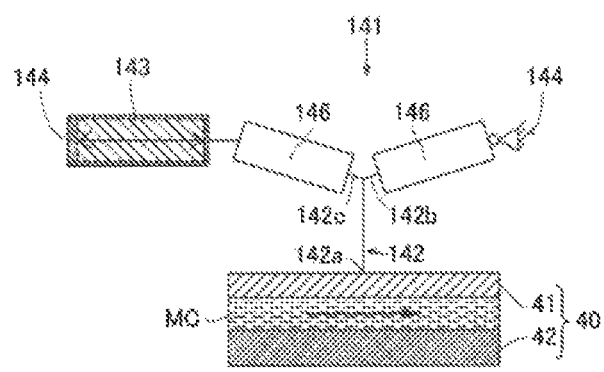
FIG. 21 is a schematic view showing another structural example of a displacement-enhancing type piezoelectric actuator.

In FIG. 21, the movable member 142 has a pressing portion 142a at the tip and support portions 142b and 142c branched in a Y shape at the other end side. One support portion 142b is supported by the fixing member 144 via an elastic hinge 146. The other support portion 142c is connected to the piezoelectric element 143 via an elastic hinge 146. In this way the movable member 142 is pressed via the elastic hinge 146, and the pressing portion 142a is displaced toward the sheet 42 side when the piezoelectric element 143 is extended.

Figure 22:
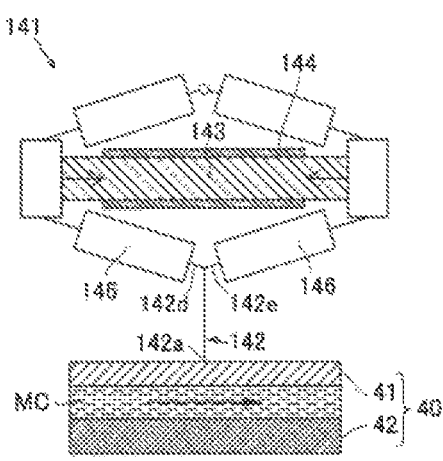
FIG. 22 is a schematic view showing a structural example of a displacement-expansion type piezoelectric actuator different from that of FIG. 21.

In FIG. 22, the movable member 142 has a pressing portion 142a at the tip and Y-shaped support portions 142d and 142e at the other end side. The pair of support portions 142d and 142e are annularly connected via a plurality of elastic hinges 146. The piezoelectric element 143 is arranged inside the annular portion, and both ends are connected to separate elastic hinges 146. In this way the movable member 142 is pressed via the elastic hinges 146 at both ends, and the pressing portion 142a is displaced toward the sheet 42 side when the piezoelectric element 143 contracts.

Specific Structural Example of Particle Sorter

A more specific structural example of the particle sorter 200 of the present embodiment will be described with reference to FIGS. 23 to 26. The micro flow path cartridge 100 installed in the particle sorter 200 will be described by taking the configurations shown in FIGS. 5 and 6 as an example.

Sample 80 is, for example, diluted and fluorescently labeled blood, and the target particle 91 is, for example, fluorescently labeled blood cells. The micro flow path cartridge 100 sorts the target cells, which are the target particles 91, from cells other non-target cells, which are the non-target particles 92. Target cells are rare cells that circulate in the blood. In the following embodiments, the target cells are circulating cancer cells (CTCs) in the blood, and the non-target cells are red blood cells, white blood cells, platelets and the like.

Installation Unit

Figure 23:
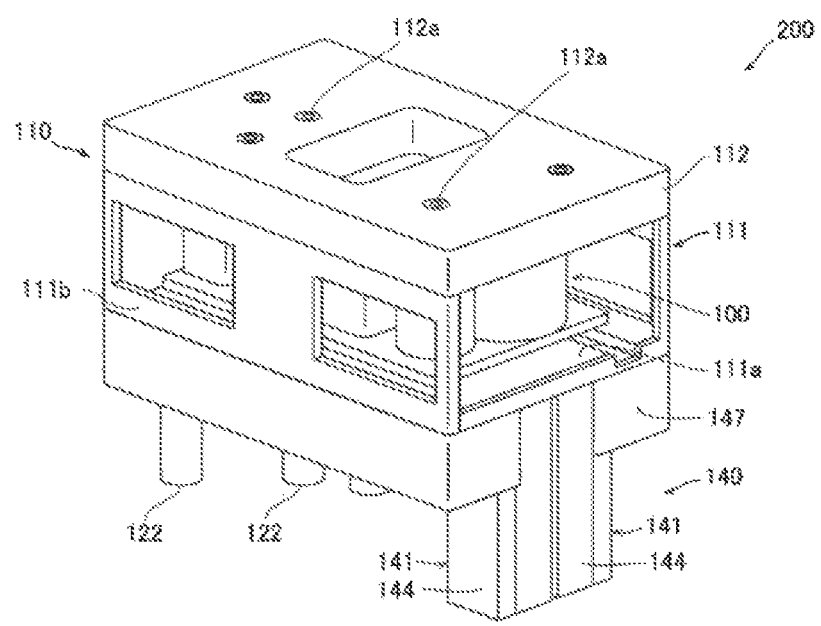
FIG. 23 is a perspective view showing a specific structural example of an installation unit and a sorting mechanism.
Figure 24:
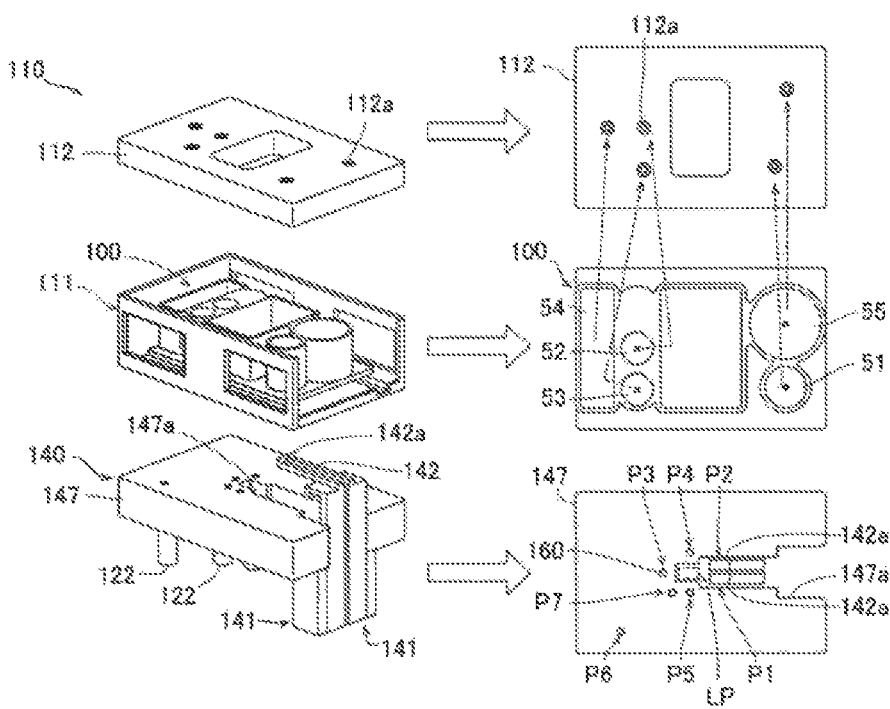
FIG. 24 is an exploded perspective view and a plan view of the installation unit and the sorting mechanism of FIG. 23.

As shown in FIGS. 23 and 24, the installation unit 110 includes a cartridge holder 111 and a cover member 112. The installation unit 110 detachably supports the micro flow path cartridge 100. The micro flow path cartridge 100 is a disposable consumable part. The micro flow path cartridge 100 is installed in the installation unit 110 by the user and is used in a sorting process. When the sorting process is completed, the micro flow path cartridge is removed from the installation unit 110. When a sorting process is performed on another sample 80, a new micro flow path cartridge 100 is installed in the installation unit 110.

The cartridge holder 111 has a bottom portion 111a that supports the peripheral edge portion of the micro flow path cartridge 100 from below. The bottom portion 111a has a frame-like shape with an opening (see FIG. 17) at the center so as to expose the formed portions of the flow path MC such as the detection region 11 and the sorting region 12 of the micro flow path cartridge 100 downward.

The cartridge holder 111 has a wall-shaped side surface portion 111b that rises upward from the outer peripheral portion of the bottom portion 111a.

The cover member 112 is detachably attached (or can be opened and closed) on the upper surface of the cartridge holder 111. The cover member 112 is provided so as to cover the upper surface opening of the liquid reservoir in the micro flow path cartridge 100 held by the cartridge holder 111. That is, the cover member 112 seals the upper surface openings of the sample chamber 52, the recovery chamber 51, the reservoir 53, the waste chamber 55, and the sheath liquid chamber 54 of the micro flow path cartridge 100. Note that a seal member for air-tightly sealing the upper surface opening is provided on the lower surface of the cover member 112.

As shown in FIG. 24, the cover member 112 is formed with one communication hole 112a for each of the sample chamber 52, the recovery chamber 51, the reservoir 53, the waste chamber 55, and the sheath liquid chamber 54. The communication hole 112a penetrates the cover member 112 in the thickness direction. Each communication hole 112a is connected to the liquid feeding unit 120 one by one on the upper surface of the cover member 112 via a pipe member 121 (see FIG. 26) described later.

A sorting mechanism 140 is provided below the installation unit 110. The sorting mechanism 140 includes a base member 147 attached to the lower surface of the cartridge holder 111, and a flow path opening/closing unit 141 provided on the base member 147. The liquid feeding unit 120 also includes a liquid feeding control valve 122 for switching the liquid flow path in the micro flow path cartridge 100 to control the liquid feeding path. These liquid feed control valves 122 are also provided on the base member 147.

The flow path opening/closing unit 141 is composed of a pinch valve provided with a displacement-enhancing piezoelectric actuator (see FIG. 17). The flow path opening/closing unit 141 is provided so as to project downward from the base member 147. The flow path opening/closing unit 141 closes the flow path MC by pressing the sheet 42, which is the lower surface of the flow path forming body 40, upward so that the pressing portion 142a pushes up from below. The flow path opening/closing unit 141 is provided one by one corresponding to the first guide path 12a and the second guide path 12b (see FIG. 25) downstream of the sorting region 12. Specifically, the two flow path opening/closing units 141 are provided so that the opening/closing position P1 of the first guide path 12a and the opening/closing position P2 of the second guide path 12b in FIG. 25 can be closed by pressing, respectively.

The liquid feed control valve 122 provided on the base member 147 is also comprised of a pinch valve that closes the flow path MC by pressing and deforming the sheet 42 of the flow path forming body 40, similar to the flow path opening/closing unit 141. Therefore, the liquid feed control valve 122 is provided so as to face upward with respect to the lower surface of the micro flow path cartridge 100. Note that the liquid feed control valve 122 is a cylinder valve of a type in which the pressing portion is operated by an air cylinder, unlike the flow path opening/closing unit 141.

A plurality of liquid feed control valves 122 are provided on the flow path MC so that the flow path of the micro flow path cartridge 100 can be switched according to the processing step.

Figure 25:
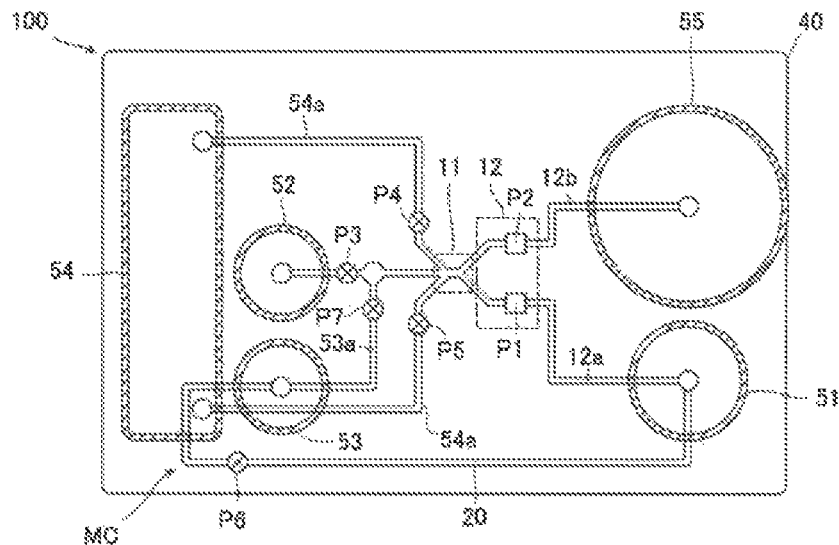
FIG. 25 is a schematic view of a flow path for describing an opening/closing position by a sorting mechanism and a switching position by a liquid feed control valve.

Specifically, as shown in FIG. 25, each liquid feed control valve 122 is provided with a switching position P3 upstream of the connection position with the connection flow path 53*a* in the first flow path 10, switching position P4 on one sheath liquid flow path 54*a* and switching position P5 on the other sheath liquid flow path 54*a*, a switching position P6 on the second flow path 20 and a switching position P7 on the connection flow path 53*a*. When the liquid feed control valve 122 at any position is turned on, the liquid feed control valve 122 presses the sheet 42 to close the corresponding flow path. When the liquid feed control valve 122 is turned off, the pressing of the sheet 42 by the liquid feed control valve 122 is released, and the corresponding flow path is opened.

Note that the liquid feed control valve 122 is not provided on the first guide path 12*a* and the second guide path 12*b*. That is, the first guide path 12*a* at the opening/closing position P1 and the second guide path 12*b* at the opening/closing position P2 are opened and closed by the corresponding flow path opening/closing units 141, respectively. The flow path opening/closing unit 141 is configured to perform not only the sorting operation but also the opening/closing of the flow path for controlling the liquid feed.

Liquid Feeding Unit

Figure 26:
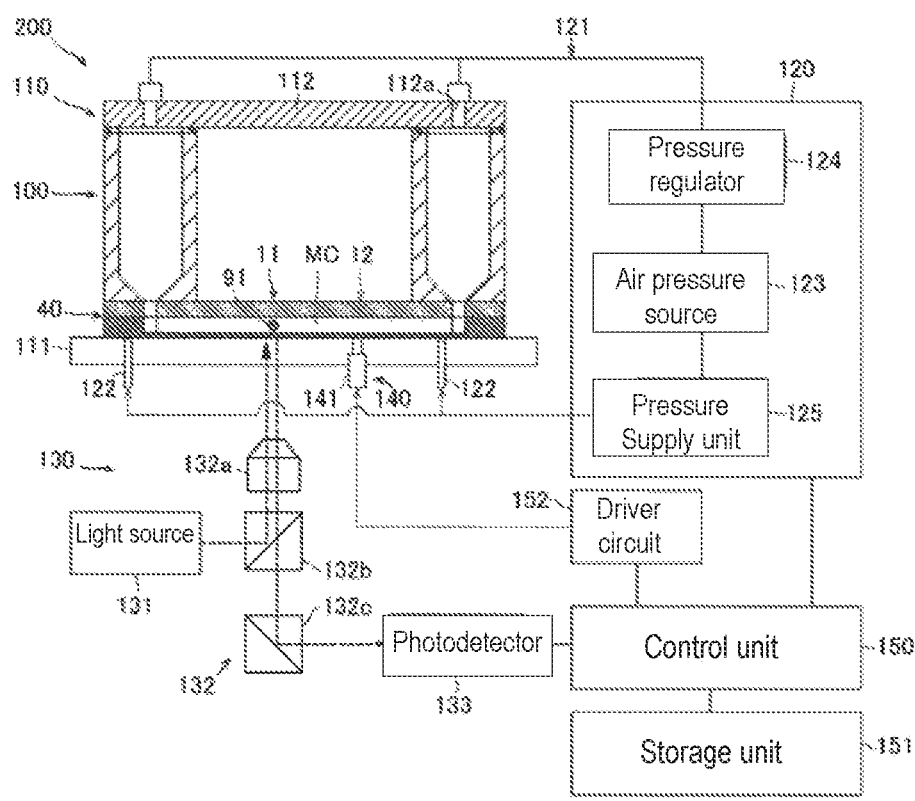
FIG. 26 is a block diagram illustrating a specific structural example of a particle sorter.

As shown in FIG. 26, the liquid feeding unit 120 is individually connected to each liquid reservoir (collection chamber 51, sample chamber 52, reservoir 53, sheath liquid chamber 54, waste chamber 55) of the micro flow path cartridge 100 via the pipe member 121. The liquid feeding unit 120 includes the plurality of liquid feeding control valves 122 described above.

The liquid feeding unit 120 is configured to supply liquid to the flow path MC of the micro flow path cartridge 100 by applying pressure under the control of the control unit 150. The liquid feeding unit 120 can individually apply positive pressure to the recovery chamber 51, the sample chamber 52, the reservoir 53, the sheath liquid chamber 54, and the waste chamber 55 to send the internal liquid to the flow path MC. The liquid feeding unit 120 can individually open the recovery chamber 51, the sample chamber 52, the reservoir 53, the sheath liquid chamber 54, and the waste chamber 55 to the atmosphere to accommodate the liquid sent from the flow path MC inside. The liquid feeding unit 120 may include an air pressure source 123 such as an air pump, a pressure regulator (regulator) 124, and a pressure supply unit 125. The liquid feeding unit 120 adjusts the liquid feeding speed from each chamber and reservoir by adjusting the pressure supplied from the air pressure source 123 by the pressure regulator 124 under the control of the control unit 150. The pressure supply unit 125 includes a multi-port valve terminal capable of individually controlling the on and off of the pressure supply to each liquid feed control valve 122. Under the control of the control unit 150, the liquid feed unit 120 individually switches the pressure supply from the air pressure source 123 on and off for each liquid feed control valve 122 by the pressure supply unit 125, so that each liquid feed control valve 122 operates individually.

Detection Unit

The detection unit 130 is provided below the installation unit 110. The detection unit 130 detects the target particles 91 from the lower surface side on which the sheet 42 is arranged in the flow path forming body 40. The detection unit 130 is configured to optically detect the target particles 91 passing through the detection region 11. Note that, as shown in FIG. 24, the base member 147 is configured with a notch-shaped penetrating portion 147*a* over a range including the detection region 11 and the sorting region 12 in which the pressing portion 142*a* is arranged. The detection unit 130 detects the target particles 91 passing through the detection region 11 from below the base member 147 via the region LP of the penetration portion 147*a*. In FIG. 26, the detection unit 130 includes a light source 131, an optical system 132, and a photodetector 133.

The light source 131 generates excitation light for the fluorescent label bound to the target particles 91. The light source 131 is composed of, for example, a semiconductor laser element.

The optical system 132 includes an objective lens 132*a* and dichroic mirrors 132*b* and 132*c*.

The photodetector 133 is configured to detect fluorescence generated from a fluorescent label excited by excitation light, and output a signal according to the fluorescence intensity. The photodetector 133 is a photon counter. For the photodetector 133, for example, a photomultiplier tube or an MPPC (multi-pixel photon counter) is used.

The excitation light emitted from the light source 131 is reflected by the dichroic mirror 132*b*, passes through the objective lens 132*a*, and irradiates the detection region 11. When the target particles 91 passing through the detection region 11 are irradiated with excitation light, fluorescence is generated from the fluorescent label. The fluorescent light passes through the objective lens 132*a* and the dichroic mirror 132*b*, is reflected by the dichroic mirror 132*c*, and is detected by the photodetector 133. When the detection unit 130 detects the fluorescence generated by irradiating the target particles 91 with the excitation light, the detection unit 130 outputs an electric signal corresponding to the detected fluorescence.

Control Unit

The control unit 150 is composed of, for example, a CPU. The control unit 150 performs various processes based on a program stored in the storage unit 151. The storage unit 151 is composed of a RAM, a ROM, a hard disk and the like.

The control unit 150 controls the liquid feeding unit 120 so that the sample chamber 52, the recovery chamber 51, the reservoir 53, the waste chamber 55, and the sheath liquid chamber 54 are individually pressurized or opened to the atmosphere. The control unit 150 switches the liquid feeding path of the liquid by controlling the liquid supply control valve 122 of the liquid supply unit 120 and the flow path opening/closing unit 141 to open and close each position on the flow path MC.

The control unit 150 is individually connected to the two flow path opening/closing units 141 via the driver circuit 152. When the pressing unit 142*a* is operated to close the flow path MC, the control unit 150 applies a predetermined operating voltage from the driver circuit 152 to the piezoelectric element 143 of the flow path opening/closing unit 141. In this way the flow path MC is closed as a result of the displacement of the pressing portion 142*a* due to the expansion and contraction operation of the piezoelectric element 143.

When the flow path MC is opened, the control unit 150 stops the voltage application from the driver circuit 152 to the piezoelectric element 143 of the flow path opening/closing unit 141. In this way the pressing portion 142a releases the pressure on the sheet 42, and the flow path MC is opened.

The control unit 150 individually controls each liquid supply control valve 122 arranged at the switching position P3 to the switching position P7 (see FIG. 25) via the pressure supply unit 125 of the liquid feeding unit 120.

The control unit 150 performs controls for carrying out the particle sorting method of the present embodiment. That is, as shown in FIG. 2, the control unit 150 controls the liquid feeding unit 120, the detection unit 130, and the sorting mechanism 140 to perform first sorting step S1, the return step S2, and the second sorting step S3. The first sorting step S1 is a step sorting the target particle-containing sample 81 by controlling the liquid feeding unit 120 so as to feed the sample 80 to the first flow path 10 of the micro flow path cartridge 100, and sorting the target particle-containing sample 81 by controlling the sorting mechanism 140 to perform a sorting operation based on the signal from the detection unit 130. The return step S2 is a step of controlling the liquid feeding unit 120 so that the target particle-containing sample 81 sorted by the first sorting step S1 is returned to the first flow path 10 via the second flow path 20. The second sorting step S3 is a step of controlling the liquid feeding unit 120 to send the returned target particle-containing sample 81 to the detection region 11 and sorting region 12 of the first flow path 10, and controlling the sorting mechanism 140 to perform a sorting operation based on the signal from the detection unit 130.

In this way the first sorting step S1 is performed on the sample 80 and the second sorting step S3 is successively performed on the target particle-containing sample 81 sorted by the first sorting step S1 within the micro flow path cartridge 100 by performing the return step S2. Note that, as shown in FIG. 8, the control unit 150 controls the liquid feeding unit 120 and the sorting mechanism 140 so as to further perform the dilution step S4.

Sorting Operation Controls

Next, the control of the sorting operation using the sorting mechanism unit 140 will be described.

As shown in FIG. 26, the control unit 150 sends liquid by the liquid feeding unit 120 and acquires a signal from the detection unit 130. Even if the non-target particles 92 are irradiated with excitation light when the non-target particles 92 in the sample 80 pass through the detection region 11, the fluorescence of a specific wavelength due to the fluorescent label of the target particles 91 does not occur. When the target particles 91 in the sample 80 pass through the detection region 11, the fluorescent label is excited by the excitation light, and the generated fluorescence of a specific wavelength is detected by the detection unit 130. As a result, as shown in FIG. 27, the signal of the detection unit 130 has a rise (peak) of the fluorescence intensity of a specific wavelength. The control unit 150 determines that the target particles 91 have been detected when the detected fluorescence intensity is equal to or higher than a preset threshold value TH. When the detected fluorescence intensity is less than the threshold value TH, the control unit 150 determines that the target particles 91 have not been detected.

As shown in FIG. 28A, when the fluorescence intensity is less than the threshold value TH, the control unit 150 closes the first guide path 12a (opening/closing position P1) by the flow path opening/closing unit 141 of the first guide path 12a, and the flow path opening/closing unit 141 of the second guide path 12b opens the second guide path 12b (opening/closing position P2). In this way the non-target particles 92 are sent to the second guide path 12b.

As shown in FIG. 28B, when the fluorescence intensity is equal to or higher than the threshold value TH, the control unit 150 causes the flow path opening/closing unit 141 of the first guide path 12a to open the first guide path 12a, and flow path opening/closing unity 141 of the second guide path 12b is closed by the flow path opening closing unit 141 of 12b. In this way the target particles 91 are sent to the first guide path 12a.

Here, the flow velocity of the sample in the first flow path 10 is controlled to a predetermined value by the liquid feeding unit 120. Therefore, the time t1 required for the target particles 91 detected in the detection region 11 to reach the sorting region 12 is known. As shown in FIG. 27, the control unit 150 controls the flow path opening/closing unit 141 to open the first guide path 12a and close the second guide path 12b at the timing when the time t1 elapses after the fluorescence intensity equal to or higher than the threshold value TH is detected. Then, the control unit 150 keeps the state in which the first guide path 12a is open and the second guide path 12b is closed for a predetermined time t2. The predetermined time t2 is a margin time for the target particles 91 that have reached the sorting region 12 to reliably pass through the opening/closing position P1 by the flow path opening/closing unit 141 based on the flow velocity in the first flow path 10.

In this way the target particles 91 are sorted into the first guide path 12a in the sorting region 12. The sample 81 containing target particles to be sorted contains sample components (that is, target particles 91, non-target particles 92, and liquid phase) that have passed through the opening/closing position P1 by the flow path opening/closing unit 141 during a predetermined time t2. When the predetermined time t2 elapses, the control unit 150 controls the flow path opening/closing unit 141 so as to close the first guide path 12a and open the second guide path 12b.

Particle Sorter Operation

Next, the flow of operation of the particle sorter 200 will be described with reference to FIGS. 29 and 30. Note that in FIGS. 29 and 30 the structures other than the micro flow path cartridge 100 shall be referred to with reference to FIGS. 23 to 26.

First, as a preliminary preparation, the user injects the sample 80 into the sample chamber 52 of the new micro flow path cartridge 100, and injects the sheath liquid into the sheath liquid chamber 54. The user installs the micro flow path cartridge 100 in the installation unit 110 and attaches the cover member 112. This prepares for the sorting process. Thereafter, the sorting process operation by the particle sorter 200 is started according to the operation input of the user.

Figure 29A:
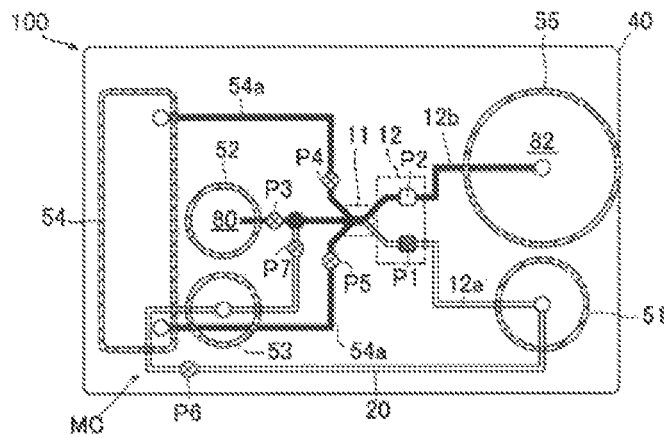
FIG. 29 is a schematic view (A) to (C) of a flow path illustrating the flow of operation of the particle sorter.
Figure 31A:
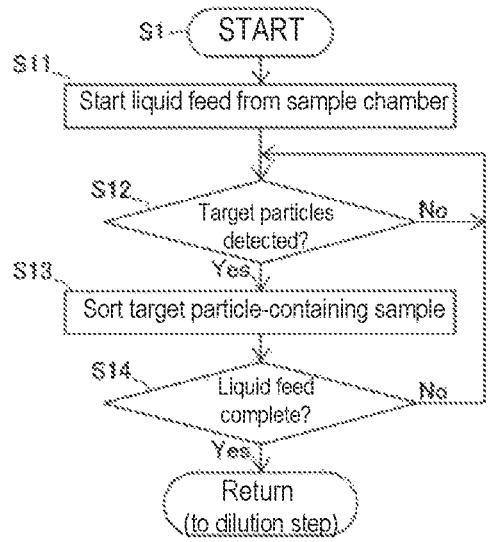
FIG. 31 is a flow chart (A) describing a first sorting step and a flow chart (B) describing a second sorting step.

The control unit 150 starts the first sorting step S1 (see FIGS. 8 and 31A). In step S11 as shown in FIG. 31A, the control unit 150 executes a process of feeding the sample 80 of the sample chamber 52 and the sheath liquid of the sheath liquid chamber 54 to the first flow path 10. Specifically, as shown in FIG. 29A, the control unit 150 causes each liquid feed control valve 122 to operate so as to open the flow paths of the switching position P3, the switching position P4, and the switching position P5, and close the flow paths of the switching position P6 and the switching position P7. The control unit 150 controls the liquid feeding unit 120 so as to apply positive pressure to the sample chamber 52 and the sheath liquid chamber 54 to open the recovery chamber 51, the waste chamber 55, and the reservoir 53 to the atmosphere. In this way the sample 80 is sent from the sample chamber 52 to the first flow path 10, and the sheath liquid is sent from the sheath liquid chamber 54 to the first flow path 10 via the sheath liquid flow path 54a. The feeding of the sample and the sheath liquid is continued until the first sorting step S1 is completed.

When the liquid feeding is started, in step S12, the control unit 150 detects the target particles 91 based on the signal of the detection unit 130. Since the liquid feeding is continued, the sample 80 flowing through the first flow path 10 passes through the detection region 11. When the target particle 91 is not detected in the detection region 11 (step S12: NO), the fluorescence intensity obtained from the signal of the detection unit 130 does not reach the threshold value TH, so that the control unit 150 closes the first guide path 12a and controls the flow path opening/closing unit 141 so as to maintain the state in which the second guide path 12b is open. The control unit 150 continues the detection process in step S12. The unsorted sample 82 is sent to the waste chamber 55 via the second guide path 12b.

Figure 29B:
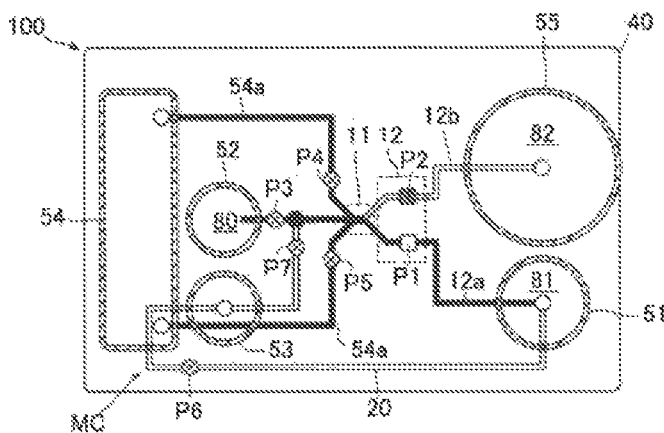

As shown in FIG. 29B, when the target particle 91 passes through the detection region 11, the fluorescence intensity obtained from the signal of the detection unit 130 becomes equal to or higher than the threshold value TH (see FIG. 27) (step S12: YES). In this case, the control unit 150 executes a process of sorting the target particle-containing sample 81 into the first guide path 12a in step S13. Specifically, the control unit 150 controls the flow path opening/closing unit 141 so as to open the first guide path 12a and close the second guide path 12b. In this way the target particle-containing sample 81 is sorted into the first guide path 12a. After the elapse of the predetermined time t2, the control unit 150 closes the first guide path 12a and switches to a state in which the second guide path 12b is opened. Next, in step S14, the control unit determines whether the entire amount of the sample 80 in the sample chamber 52 has been sent to the first flow path 10. If the entire amount of the sample 80 in the sample chamber 52 has been sent to the first flow path 10 (step S14: YES), the process proceeds to step S4 (see FIG. 8). If the entire amount of the sample 80 in the sample chamber 52 has not been sent to the first flow path 10 (step S14: NO), the process is returned to step S12. Note that to determine whether the entire amount of the sample 80 in the sample chamber 52 has been sent to the first flow path 10, the time required for sending the entire amount of liquid is calculated from the volume of the sample and the liquid feeding speed can be determined beforehand, then determined whether the elapsed time from the start of liquid feeding of the sample has reached the calculated time.

In this way the first sorting step S1 is performed. The first sorting step S1 is carried out until the total amount of the sample 80 in the sample chamber 52 has been transferred. After the completion of the first sorting step S1, all the target particle-containing sample 81 sorted into the first guide path 12a is stored in the recovery chamber 51.

Figure 29C:
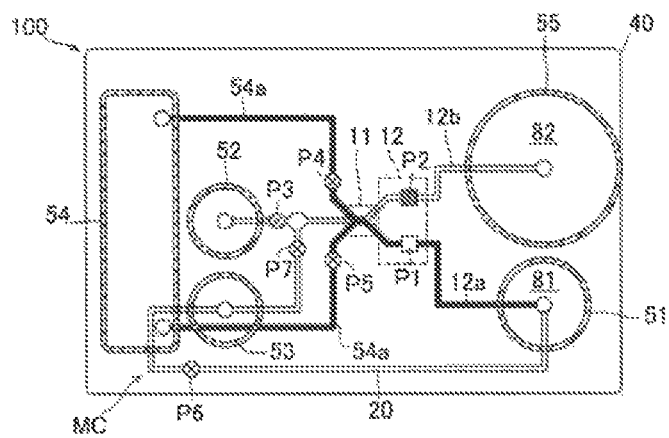

Next, the control unit 150 performs a dilution step S4 (see FIG. 8) for diluting the target particle-containing sample 81 by sending the sheath liquid to the recovery chamber 51. Specifically, as shown in FIG. 29C, the control unit 150 causes each liquid feed control valve 122 to operate to open the flow paths of the switching position P4 and the switching position P5, and close the flow paths of the switching position P3, the switching position P6, and the switching position P7. The control unit 150 controls the flow path opening/closing unit 141 so as to maintain the state in which the first guide path 12a is open and the second guide path 12b is closed. The control unit 150 controls the liquid supply unit 120 so as to apply a positive pressure to the sheath liquid chamber 54 to open the sample chamber 52, the recovery chamber 51, the waste chamber 55, and the reservoir 53 to the atmosphere. In this way the sheath liquid from the sheath liquid chamber 54 is sent to the recovery chamber 51 through the sheath liquid flow path 54a, the detection region 11, and the first guide path 12a. The control unit 150 continues to send the sheath liquid at a predetermined flow rate for a predetermined time, so that a preset amount of the sheath liquid is accommodated in the recovery chamber 51 as a diluted liquid. As a result, the target particle-containing sample 81 is diluted to a predetermined concentration. Note that the dilution step S4 may be executed before the first sorting step S1. In this way the target particle-containing sample 81 and the sheath liquid can be mixed more effectively in the recovery chamber 51.

Figure 30D:
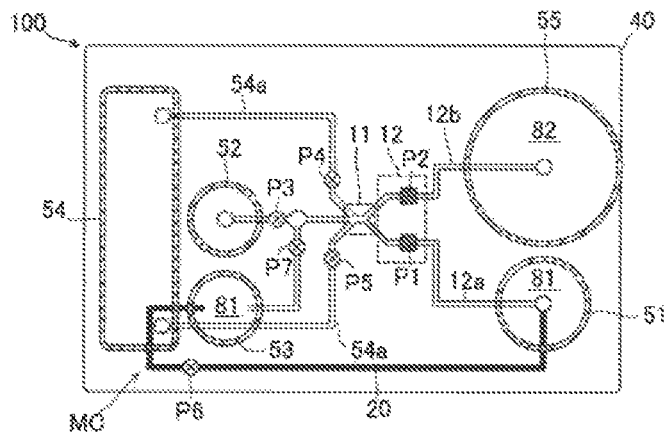
FIG. 30 is a schematic view (D) to (F) of a flow path illustrating the flow of operation of the particle sorter.

Next, the control unit 150 carries out the return step S2 (see FIG. 8). In step S2, the control unit 150 controls the liquid feeding unit 120 so that the diluted target particle-containing sample 81 in the recovery chamber 51 is returned upstream of the detection region 11 of the first flow path 10. Specifically, as shown in FIG. 30D, the control unit 150 causes each liquid feed control valve 122 to operate to open the flow path at the switching position P6 and close the flow paths at the switching position P3, the switching position P4, the switching position P5, and the switching position P7. The control unit 150 controls the flow path opening/closing unit 141 so as to close the first guide path 12a. The control unit 150 applies a positive pressure to the recovery chamber 51 to control the liquid supply unit 120 so as to open the sample chamber 52, the sheath liquid chamber 54, the waste chamber 55, and the reservoir 53 to the atmosphere. In this way the diluted target particle-containing sample 81 in the recovery chamber 51 is sent to the reservoir 53 through the second flow path 20. The control unit 150 causes the entire amount of the target particle-containing sample 81 in the recovery chamber 51 to be stored in the reservoir 53. Note that the time required to feed all the liquid in the recovery chamber 51 can calculated beforehand from the storage capacity of the recovery chamber 51 and the liquid feed velocity, and the total amount of the liquid in the recovery chamber 51 may be sent from the recovery chamber 51 for a period longer than the calculated time in order to store the entire amount of the diluted target particle-containing sample 81 in the recovery chamber 51 to the reservoir 53.

Figure 30E:
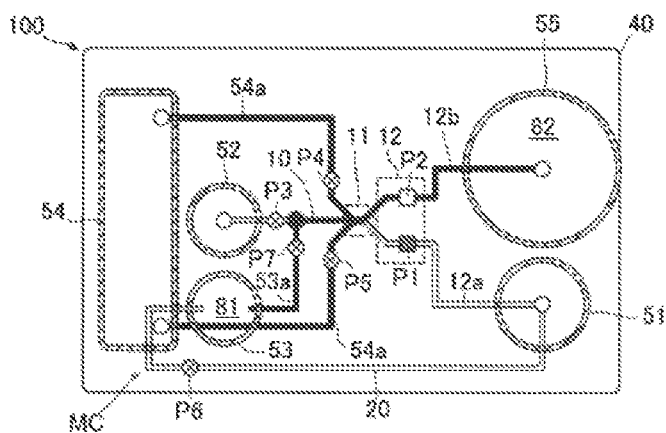
Figure 31B:
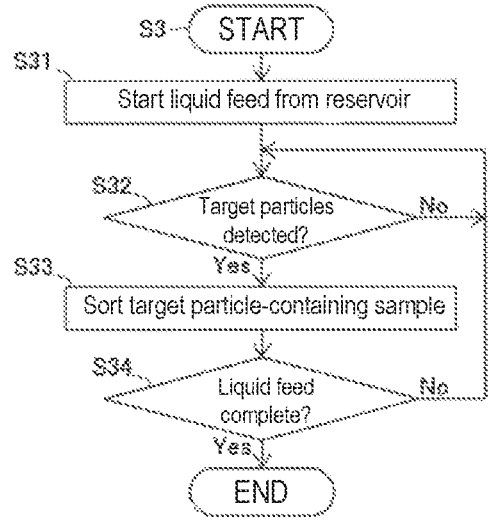

Next, the control unit 150 starts the second sorting step S3 (see FIGS. 8 and 31B). In step S31 as shown in FIG. 31B, the control unit 150 executes a process of feeding the target particle-containing sample 81 of the reservoir 53 and the sheath liquid of the sheath liquid chamber 54 to the first flow path 10. Specifically, as shown in FIG. 30E, the control unit 150 causes each liquid feed valve 122 to operate to open the flow paths of the switching position P4, the switching position P5, and the switching position P7, and close the flow paths of the switching position P3 and the switching position P6. The control unit 150 controls the liquid supply unit 120 so as to apply positive pressure to the reservoir 53 and the sheath liquid chamber 54 to open the sample chamber 52, the recovery chamber 51, and the waste chamber 55 to the atmosphere. In this way the target particle-containing sample 81 is sent from the reservoir 53 to the first flow path 10 via the connection flow path 53a, and the sheath liquid is sent from the sheath liquid chamber 54 to the first flow path 10 via the sheath liquid flow path 54a.

Figure 30F:
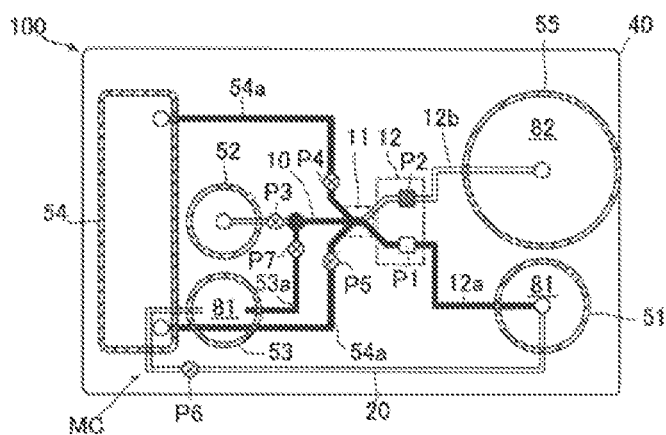

The content of the detection and sorting operations in the second sorting step S3 are the same as those in the first sorting step S1. That is, as shown in FIG. 31B, the control unit 150 executes the detection process (step S32), the sorting process (step S33), and the total liquid feed determination process (step S34). The detection process (step S32), the sorting process (step S33), and the total liquid feed determination process (step S34) are the same processes of step S12, step S13, and step S14 in the first sorting step S1 of FIG. 31A, respectively, detailed description thereof will be omitted. As shown in FIG. 30F, when the target particle 91 is detected in the detection region 11 and the fluorescence intensity obtained from the signal of the detection unit 130 becomes equal to or higher than the threshold value TH, the control unit 150 controls the flow path opening/closing unit 141 so as to open the first guide path 12a and close the second guide path 12b. When the fluorescence intensity is less than the threshold value TH, the control unit 150 switches to a state in which the first guide path 12a is closed and the second guide path 12b is opened. In this way the target particle-containing sample 81 is again dispensed into the first guide path 12a.

The second sorting step S3 is carried out until the total amount of the target particle-containing sample 81 in the reservoir 53 has been transferred. After the completion of the second sorting step S3, all the target particle-containing samples 81 resorted into the first guide path 12a are stored in the recovery chamber 51.

Note that in the target particle-containing sample 81 flowing through the first flow path 10, the number of non-target particles 92 is significantly reduced as compared with the sample 80 in the first sorting step S1. Therefore, in the second sorting step S3, the non-target particles 92 mixed in the target particle-containing sample 81 are further removed, and the purity of the target particles 91 in the target particle-containing sample 81 is increased.

Here, the liquid feeding velocity in the second sorting step S3 may be the same as the liquid feeding velocity in the first sorting step S1, or may be different from the liquid feeding velocity in the first sorting step S1. For example, the control unit 150 may control the liquid feeding unit 120 so that the flow velocity of the sample in the first sorting step S1 is greater than the flow velocity of the target particle-containing sample 81 in the second sorting step S3. In other words, the flow velocity of the target particle-containing sample 81 in the second sorting step S3 may be lower than the flow velocity of the sample in the first sorting step S1. The flow velocity of the target particle-containing sample 81 can be adjusted by controlling the pressure regulator 124 and changing the magnitude of the positive pressure supplied to the first flow path 10.

In this way the first sorting step S1 can be completed in a short time. Then, in the second sorting step S3 for the target particle-containing sample 81 whose purity of the target particles 91 has been increased by the first sorting step S1, the sorting accuracy can be improved by feeding the liquid at a relatively low flow velocity. As a result, the purity of the target particles can be effectively improved while shortening the time required for sorting.

As described above, the target particle 91 is sorted by the particle sorter 200 of the present embodiment. In the above description, an example is shown in which the first sorting step S1 and the second sorting step S3 are performed a total of two sorting steps, but the sorting step may be performed three or more times. The third and subsequent sorting steps are a repetition of the dilution step S4, the return step S2, and the second sorting step S3.

EXAMPLES

Next, the results of various experiments performed for verification of the particle sorter of the present embodiment will be described.

Examples

The purity of the target particles 91 and required time were measured when a first sorting process and a second sorting process (that is, a total of two sorting steps) were performed by the particle sorter of the embodiment using the micro flow path cartridge 100 shown in FIG. 25.
Sample and Sheath Liquid As described below, samples were prepared by regarding different types of fluorescent beads as target particles 91 and non-target particles 92.

Target particles: Green fluorescent beads (15 μm in diameter, manufactured by Thermo Scientific)

Non-target particles: Red fluorescent beads (3.2 μm in diameter, manufactured by Thermo Scientific)

Sheath liquid: Ultrapure water containing 2% surfactant

The volume of the sample, the concentration and number of total particles (total of target particles and non-target particles), the number of target particles, and the purity of the target particles are shown in Table 1 below.

TABLE 1

| | Example Before-sorting sample | | | |
|---|---|---|---|---|
| | Total particles | | Target particles | |
| Volume [μL] | Concentration [particles/mL] | Quantity [particles] | Quantity [particles] | Purity [%] |
| 100 | $1.17 \times 10^8$ | $1.17 \times 10^7$ | 653 | 0.0056 |

Note that the purity of the target particles=(number of target particles/total number of particles). The purity (0.0056%) of the target particles in the sample assumes a sorting process using rare particles having an extremely small content in the sample, such as CTC in the blood sample, as the target particles.

After injecting the sample and the sheath liquid into the sample chamber 52 and the sheath liquid chamber 54 of the micro flow path cartridge 100, respectively, the sorting process by the particle sorter 200 (first sorting step, dilution step, return step, and second sorting step) was carried out under the following conditions.
Experimental Conditions Sample flow rate: 12.2 μL/min (set value)

Sheath fluid flow velocity: 130 μL/min

Sampling rate of detection unit: 100 kHz

Switching speed of flow path opening/closing unit: 310 Hz

Amount of sheath liquid added in the dilution step: 200 μL

Note that the flow velocity was the same in the first sorting step and the second sorting step.

The results of the sorting process (after the first sorting step and the second sorting step) according to the examples are shown in Table 2 below. Note that the number of particles is the result of measuring the recovered target particle-containing sample with a flow cytometer.

TABLE 2

Example

After 1st and 2nd sorting steps

| Total particles Quantity [particles] | Target particles Quantity [particles] | Purity [%] | Recovery rate [%] | Processing time [sec] | Throughput [event/sec] |
|---|---|---|---|---|---|
| 2012 | 518 | 25.7 | 79.2 | 1442 | 8114 |

As a result of the two sorting steps (first sorting step and second sorting step) according to the examples, the purity of the target particles was 25.7% and processing time was 1442 seconds. From Tables 1 and 2, it can be seen that the target particles were concentrated about 4600 times from the purity of the target particles (0.0056%) in the before-sorting sample to the purity of 25.7%. The recovery rate of the target particles was about 80%. In addition, throughput was calculated as an evaluation index for processing efficiency. Throughput=(total number of processed particles/processing time). The sorting for each particle is called an event. The throughput of the examples was 8114 (events/sec).

Comparative Example 1 and Comparative Example 2

Next, the time required to obtain a purity equivalent to the purity (25.7%) of the example was measured in a one-time sorting step as Comparative Example 1 and Comparative Example 2.

For comparison with the Example, in Comparative Example 1 and Comparative Example 2, only one sorting step was carried out using the same micro flow path cartridge as in Example. Therefore, in Comparative Example 1 and Comparative Example 2, the second flow path 20 and the reservoir 53 are not used. The particle sorter 200 used in Comparative Example 1 and Comparative Example 2 was also the same as in the above-mentioned Example.

Sample and Sheath Liquid

The particles and sheath liquid used in Comparative Example 1 and Comparative Example 2 are the same as those in the above-mentioned Example.

Experimental Conditions

Sample flow rate: 10.5 μL/min (set value)

Sheath fluid flow velocity: 130 μL/min

Sampling rate of detection unit: 100 kHz

Switching speed of flow path opening/closing unit: 310 Hz

Table 3 below shows the volume of the sample, the concentration and number of total particles (total of target particles and non-target particles), the number of target particles, and the purity of the target particles in Comparative Example 1 and Comparative Example 2.

TABLE 3

Comparative Example

Before-sorting sample

| | Volume [μL] | Total particles Concentration [particles/mL] | Total particles Quantity [particles] | Target particles Quantity [particles] | Purity [%] |
|---|---|---|---|---|---|
| Comp. Ex. 1 Comp. Ex. 2 | 100 | $1.051 \times 10^6$ | $1.051 \times 10^5$ | 613 | 0.58 |

Here, in Comparative Example 1 and Comparative Example 2, the concentration of the total particles was diluted to 1/100 as compared with the above-mentioned Example. The purity of the target particles in the before-sorting sample was 0.58%.

The results of the sorting process according to Comparative Example 1 and Comparative Example 2 are shown in Table 4 below.

TABLE 4

Comparative Example

After sorting step (one sort only)

| | Total particles Quantity [particles] | Target particles Quantity [particles] | Purity [%] | Recovery rate [%] | Processing time [sec] | Throughput [event/sec] |
|---|---|---|---|---|---|---|
| Comp. Ex. 1 | 1824 | 536 | 29.4 | 87.4 | 343 | 306 |
| Comp. Ex. 2 | 1594 | 604 | 37.9 | 98.5 | 570 | 185 |

In Comparative Example 1, the purity of the target particles was 29.4%, and in Comparative Example 2, the purity of the target particles was 37.9%. Therefore, in Comparative Example 1 and Comparative Example 2, almost the same results as those in the above-mentioned Examples were obtained with respect to the purity of the sorted target particles.

In Comparative Example 1, the processing time was 343 seconds, and in Comparative Example 2, the processing time was 570 seconds. The throughput of Comparative Example 1 was 306 (event/sec), and the throughput of Comparative Example 2 was 185 (event/sec).

Considerations

Figure 32:
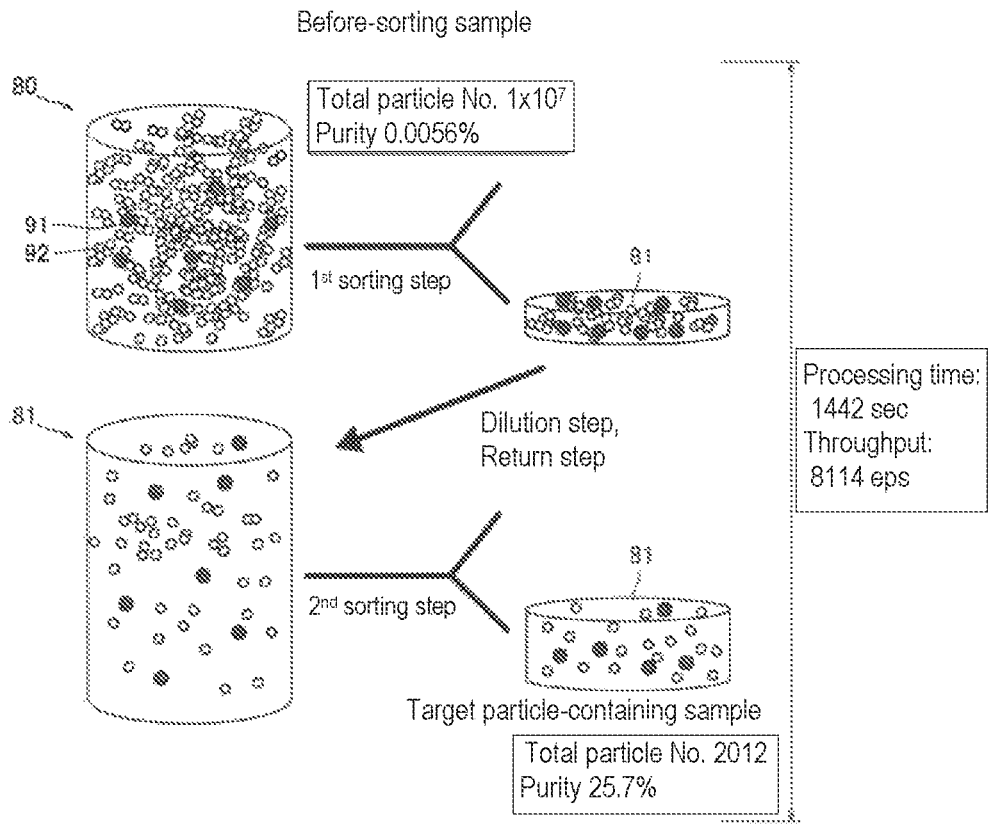
FIG. 32 is a diagram showing the result of the sorting process according to an embodiment.
Figure 33:
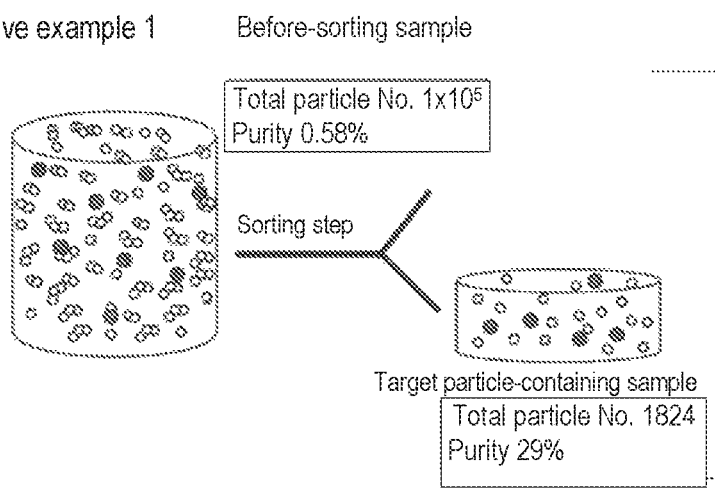
FIG. 33 is a diagram showing the result of the sorting process according to Comparative Example 1.

As shown in FIG. 32, in the above-mentioned example, it took 1442 seconds to obtain a target particle-containing sample having a purity of 25.7% from the sample having a before-sorting purity of 0.0056%. On the other hand, in Comparative Example 1 (see FIG. 33), it took 343 seconds to obtain a target particle-containing sample having the same purity as that of the Example from a sample having a before-sorting purity of 0.58%, which was 100 times that of Example. In Comparative Example 2, it took 570 seconds.

As described above, in Comparative Example 1 and Comparative Example 2, it was necessary to increase the number of non-target particles 100 times in order to make the purity of the target particles equivalent to that of the above-mentioned Example. In order to process the total amount of the sample (purity of 0.0056%) used in the above Example so that the same results can be obtained by the methods of Comparative Examples 1 and 2, the volume of the sample is 100 times as large as that of the simple calculation and, hence, the processing time required for this is 100 times longer. That is, in the case of Comparative Example 1, a processing time of 34,300 seconds is required. Hence, in the above-mentioned Example (1442 seconds), when the same before-sorting sorting is processed to the same degree of purity, the time required for the sort is reduced to about 1/24 as compared with Comparative Example 1 (34300 seconds).

Figure 34:
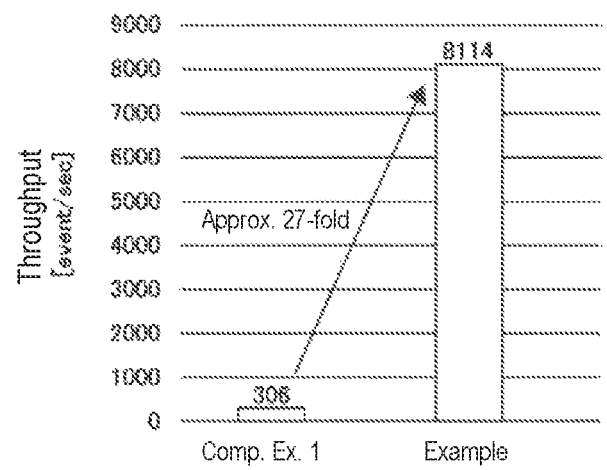
FIG. 34 is a graph comparing the throughputs of the sorting process between Example and Comparative Example 1.

Throughput is a simple example of this result. It can be seen that in the above embodiment, 8114 particles are processed per second, whereas in Comparative Example 1, only 306 particles are processed per second, and in Comparative Example 2, only 185 particles are processed per second. As shown in FIG. 34, the throughput of the Example is about 27 times that of the Comparative Example 1. From the above, it was confirmed that the particle sorter 200, the particle sorting method, and the micro flow path cartridge 100 of the present embodiment can shorten the time required for sorting the target particles with sufficient purity.

Comparative Example 3

The result of investigating the relationship between the purity of the target particles and the throughput in the sorting process will be described.

In Comparative Example 3, as shown in Table 5 below, the sorting process was performed only once using three types of before-sorting samples (Sample 1, Sample 2, and Sample 3) in which the ratio of the target particles was adjusted to a constant value and the concentrations of the total particles were different were used. For each sample, the experimental conditions of the sorting step are the same as those of Comparative Example 1 and Comparative Example 2.

TABLE 5

| | Comparative Example 3 | | |
|---|---|---|---|
| | Sample 1 | Sample 2 | Sample 3 |
| Total particle concentration [particles/mL] | 603310 | 301655 | 150827 |
| Target particle ratio [%] | 0.53% | 0.53% | 0.53% |
| Volume [µL] | 200 | 400 | 800 |
| Processing time [sec] | 326 | 717 | 1221 |
| Throughput [event/sec] | 370 | 168 | 99 |
| Purity [%] | 26.8 | 57.6 | 80.3 |

Sample 2 is a 2-fold dilution of Sample 1. Sample 3 is a 2-fold dilution of Sample 2. Since the samples diluted 2-fold are processed under the same experimental conditions, the throughput of sample 2 is about ½ that of sample 1 and that of sample 3 is about ½ that of sample 2. As can be seen from Table 5, the purity of Sample 1 was 26.8%, that of Sample 2 was 57.6%, and that of Sample 3 was 80.3%.

Considerations

Figure 35:
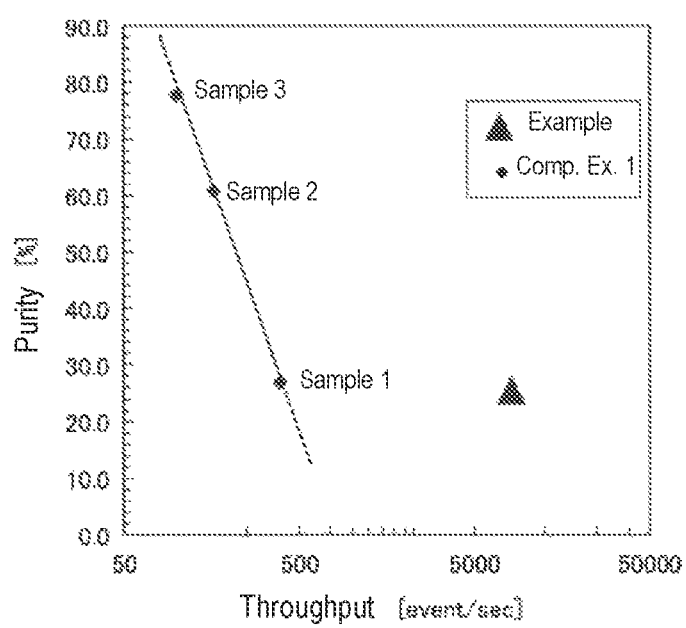
FIG. 35 is a graph showing the relationship between throughput and purity in Example and Comparative Example 3.
Figure 36:
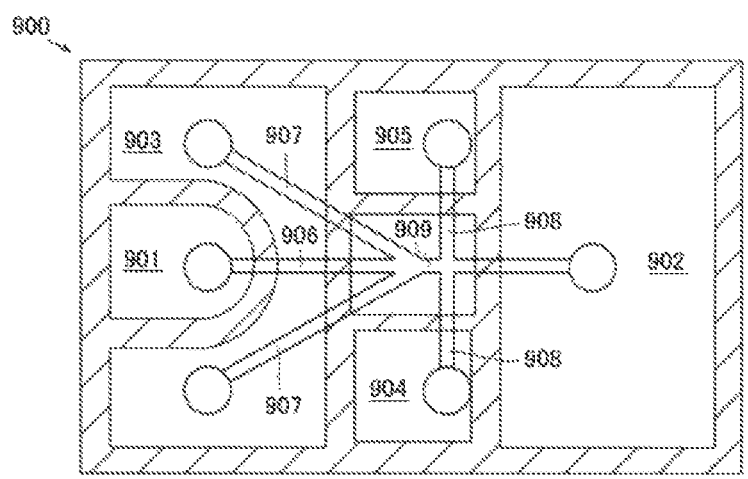
FIG. 36 is a diagram showing a conventional art.

A graph plotting the relationship between the throughput and the obtained purity for Samples 1 to 3 is shown in FIG. 35. In FIG. 35, the vertical axis is the purity of the target particles and the horizontal axis is the throughput. From FIG. 35, it can be seen that there is a trade-off relationship between the throughput of the sorting process and the purity of the target particles. That is, in the micro flow path cartridge that performs the sorting process only once, such as the interchangeable flow path cartridge 900 of FIG. 36, the trade-off relationship as shown in FIG. 35 is established between the throughput and the purity. It can be seen that it is difficult to increase the throughput (processing speed) beyond this relationship.

FIG. 35 also plots the results of the above embodiment using the micro flow path cartridge 100 of this embodiment. From FIG. 35, it was confirmed that in the present embodiment, processing with high throughput, which cannot be achieved by only one sorting process, is possible. In this way according to the present embodiment the particle sorter 200, the particle sorting method, and the micro flow path cartridge 100 of the present embodiment were confirmed to reduce the processing time that cannot be achieved by performing the sorting process only once.

In addition to this, the present embodiment has the following advantages.

Consider performing the sorting step a plurality of times similar to the Examples by the user collecting the target particle-containing sample obtained by using the replaceable flow path cartridge 900 (see FIG. 36), which performs the sorting process only once, by a pipette or the like, and injecting that sample again into the replaceable flow path cartridge 900. However, in this case, since it is necessary to take out the sample to the outside of the cartridge, contamination and human error may occur. In addition, the target particles may be damaged due to pipetting. On the other hand, in the present embodiment, since the plurality of sorting steps are completed only inside the micro flow path cartridge 100, contamination and human error due to taking out the sample to the outside can be prevented. Moreover, since pipetting is not required, damage to the target particles is suppressed. This can be said to be a great merit especially when performing the sorting process using cells or the like as the target particles 91.

FACS (Fluorescence assisted cell sorting) using a flow cytometer is another method of particle sorting. While FACS can achieve high throughput, it has disadvantages in that the damage to particles in the sorting process is great and the process is performed in an open environment, so that there is a risk of contamination. On the other hand, in the present embodiment, since the sorting mechanism unit 140 performs sorting by opening and closing the flow path, damage to the particles can be suppressed. Also, since the sorting process is executed only inside the micro flow path cartridge 100, the occurrence of contamination can be prevented.

It should be noted that the embodiments disclosed herein are exemplary in all respects and are not considered to be restrictive. The scope of the present invention is indicated not by the description of the above embodiments but by the scope of the claims, and includes meanings equivalent to the claims and all changes within the scope thereof.

For example, although the liquid feeding unit 120, the detection unit 130, the sorting mechanism 140, the control unit 150, the storage unit 151, and the driver circuit 152 are provided separately from the micro flow path cartridge 100 in the above-described embodiment, at least part of these also may be incorporated in the micro flow path cartridge 100. For example, the light source 131, the optical system 132, and the photodetector 133 that configure the detection unit 130 may be incorporated in the micro flow path cartridge 100, or the photodetector 133 may be incorporated. The sorting mechanism 140 may be incorporated in the micro flow path cartridge 100, the flow path opening/closing unit 141 configuring the sorting mechanism unit 140 may be incorporated, or the liquid feed control valve 122 may be incorporated.

What is claimed is:

1. A particle sorter comprising:
a micro flow path cartridge including a first flow path, a second flow path, and a third flow path,
an installation part,
a liquid feeder,
a detector,
a sorting device, and
a controller, wherein:
the first flow path comprises:
a detection region where the detector is located to detect target particles contained in a sample, and
a sorting region disposed to receive flow from the detection region, the sorting region having at least two flow paths, the sorting region where the sorting device is located for obtaining a target particle-containing sample containing the detected target particles,
one end of the second flow path connects to the detection region, and the other end of the second flow path is configured to obtain the target particle-containing sample for returning the target particle-containing sample to the detection region, and
one end of the third flow path connects to the detection region, and the other end of the third flow path is configured to obtain other sample that is not the target particle-containing sample for returning the other sample to the detection region;
the installation part comprises a cartridge holder for supporting the micro flow path cartridge;
the liquid feeder comprises a pressure regulator for providing pressure to drive liquid in the micro flow path cartridge via the first flow path;
the detector is configured to output a signal corresponding to the target particle passing through the detection region;
the sorting device is configured to perform a sorting operation for obtaining the target particle-containing sample in the sorting region based on the signal from the detector, and the sorting device comprises a flow path opening/closing unit that opens and closes at least one of the flow paths in the sorting region of the first flow path; and
the controller is in communication with the liquid feeder and the sorting device, wherein:
the controller is programmed to control the liquid feeder such that the target particle-containing sample obtained in the sorting region is returned to the detection region via the second flow path, and
the controller is programmed to control the sorting device to perform the sorting operation on the returned target particle-containing sample.

2. The particle sorter according to claim 1, wherein the controller is further programmed to execute:
a first sorting process of controlling the liquid feeder so that the sample is fed to the first flow path of the micro flow path cartridge and of controlling the sorting device to obtain the target particle-containing sample by performing the sorting operation based on the signal from the detector;
a return process of controlling the liquid feeder so that the target particle-containing sample obtained by the first sorting process is returned to the first flow path via the second flow path; and
a second sorting process of controlling the liquid feeder so that the returned target particle-containing sample is fed to the detection region and the sorting region of the first flow path, and of controlling the sorting device to perform the sorting operation based on the signal from the detector.

3. The particle sorter according to claim 2, wherein
the controller is further programmed to control the liquid feeder so that flow velocity of the sample in the first sorting process is greater than flow velocity of the target particle-containing sample in the second sorting process.

4. The particle sorter according to claim 1, wherein
the controller is further programmed to control the liquid feeder so as to dilute the target particle-containing sample and is programmed to control the sorting device to perform a sorting operation on the diluted target particle-containing sample.

5. The particle sorter according to claim 4, wherein
the micro flow path cartridge further comprises a recovery chamber configured to collect the target particle-containing sample; and
the controller is further programmed to control the liquid feeder so as to dilute the target particle-containing sample within the recovery chamber.

6. The particle sorter according to claim 5, wherein
the controller is further programmed to control the liquid feeder so as to dilute the target particle-containing sample within the recovery chamber by sending the target particle-containing sample to the recovery chamber that stores a diluting liquid.

7. The particle sorter according to claim 1, wherein
the micro flow path cartridge further comprises:
a sample chamber for storing the sample to be sent to the first flow path,
a reservoir communicating with the second flow path, and
a connecting flow path connecting the reservoir and the detection region of the first flow path; and
the controller is further programmed to control the sorting device so as to obtain the target particle-containing sample from the sample sent from the sample chamber to the first flow path, and is programmed to control the liquid feeder so that the target particle-containing sample is returned to the first flow path via the second flow path, the reservoir and the connecting flow path.

8. The particle sorter according to claim 1, wherein
the micro flow path cartridge further comprises a sample chamber for storing a sample to be fed to the first flow path; and
the controller is further programmed to control the liquid feeder so as to obtain the target particle-containing sample from the sample sent from the sample chamber to the first flow path, and return the target particle-containing sample to the first flow path via the second flow path and the sample chamber.

9. The particle sorter according to claim 1, wherein
the controller is further programmed to control the liquid feeder so as to return the sample that was not obtained as the target particle-containing sample in the sorting region of the first flow path to the detection region of the first flow path via the third flow path and to feed the returned sample to the detection region of the first flow path, and is programmed to control the sorting device to perform the sorting operation based on the signal from the detector.

10. The particle sorter according to claim 1, wherein
the micro flow path cartridge further comprises a recovery chamber for collecting the obtained target particle-containing sample, and wherein the sorting region of the first flow path is configured so as to branch the first flow path into a first guide path that guides the target particle-containing sample to the recovery chamber and a second guide path different from the first guide path; and the controller is further programmed to control the sorting device so as to guide the target particle-containing sample to the first guide path.

11. The particle sorter according to claim 1, wherein the flow path opening/closing unit comprises a pinch valve, and is configured to close at least one of the flow paths in the sorting region via deformation by pressing a region of the micro flow path cartridge in which at least one of the flow paths is formed.

12. The particle sorter according to claim 11, wherein the flow path opening/closing unit comprises a displacement-enhancing piezoelectric actuator.

13. The particle sorter according to claim 12, wherein the displacement-enhancing piezoelectric actuator comprises:
a movable member having a pressing part facing a pressing position of the micro flow path cartridge,
a piezoelectric element for moving the movable member, and
a fixing member for holding the piezoelectric element and the movable member; and the movable member is configured to displace the pressing part with a displacement amount larger than a displacement amount of the piezoelectric element.

14. The particle sorter according to claim 1, wherein the first flow path and the second flow path have:
a depth of 1 μm or more and 1000 μm or less, and
a width of 1 μm or more and 1000 μm or less.

* * * * *